US011534073B2

(12) United States Patent
Hamaguchi et al.

(10) Patent No.: US 11,534,073 B2
(45) Date of Patent: Dec. 27, 2022

(54) BLOOD PRESSURE MEASURING DEVICE

(71) Applicants:OMRON HEALTHCARE CO., LTD., Muko (JP); OMRON CORPORATION, Kyoto (JP)

(72) Inventors: Takehiro Hamaguchi, Kyoto (JP); Takeshi Kubo, Kyoto (JP); Yoshihiko Sano, Kyoto (JP); Takanori Nishioka, Kyoto (JP); Kentaro Mori, Kyoto (JP); Yu Higashimura, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 81 days.

(21) Appl. No.: 16/913,811

(22) Filed: Jun. 26, 2020

(65) Prior Publication Data

US 2020/0323447 A1 Oct. 15, 2020

Related U.S. Application Data

(63) Continuation of application No. PCT/JP2018/046234, filed on Dec. 17, 2018.

(30) Foreign Application Priority Data

Dec. 28, 2017 (JP) .............................. JP2017-253065

(51) Int. Cl.
*A61B 5/022* (2006.01)
*A61B 5/0235* (2006.01)
*A61B 5/00* (2006.01)

(52) U.S. Cl.
CPC ........ *A61B 5/02233* (2013.01); *A61B 5/0235* (2013.01); *A61B 5/681* (2013.01); *A61B 2562/0219* (2013.01)

(58) Field of Classification Search
CPC . A61B 5/02233; A61B 5/681; A61B 5/02141; A61B 5/022; A61B 5/02225;
(Continued)

(56) References Cited

U.S. PATENT DOCUMENTS 6,336,901 B1   1/2002  Itonaga et al.
6,636,901 B2 * 10/2003  Sudhakaran .............. G06F 9/52
                                                                 710/200

(Continued)

FOREIGN PATENT DOCUMENTS

JP   H11-309119 A   11/1999
JP   2007-175185 A   7/2007
(Continued)

OTHER PUBLICATIONS

Feb. 12, 2019 Search Report issued in International Patent Application No. PCT/JP2018/046234.

*Primary Examiner* — Daniel L Cerioni
*Assistant Examiner* — Deirdre M Willgohs
(74) *Attorney, Agent, or Firm* — Oliff PLC

(57) ABSTRACT

A blood pressure measuring device includes a device main body; a curler configured to bend along a circumferential direction of a wrist of a living body, and configured to come into contact with a portion of the wrist at least between a dorsal side and a palmar side; a strap on the device main body, configured to cover an outer surface of the curler; a sensing cuff arranged in a region of the wrist where arteries exist; a rubber plate on a side of the sensing cuff nearer to the curler and configured to elastically deform; a pressing cuff between the curler and the rubber plate and configured to press the sensing cuff; and a cuff on a side of the curler nearer to the living body and arranged on the dorsal side of the wrist.

2 Claims, 22 Drawing Sheets

(58) Field of Classification Search
CPC ..... A61B 5/6824; A61B 5/021; A61B 5/0235; A61B 2562/0247; A61B 2562/0219; A61B 5/6801; A61B 5/6802; A61B 5/6813; A61B 2562/02
USPC ................ 600/499, 495, 490, 492, 493, 494
See application file for complete search history.

(56) References Cited

U.S. PATENT DOCUMENTS

| | | | |
|---|---|---|---|
| 7,153,270 B2* | 12/2006 | Sano | A61B 5/02233 600/499 |
| 2006/0135872 A1* | 6/2006 | Karo | A61B 5/02233 600/499 |
| 2009/0234381 A1 | 9/2009 | Karo | |
| 2014/0187987 A1 | 7/2014 | Fraden et al. | |
| 2018/0177414 A1 | 6/2018 | Tokko et al. | |
| 2018/0199830 A1* | 7/2018 | Basu | A61B 5/6843 |

FOREIGN PATENT DOCUMENTS

| | | |
|---|---|---|
| JP | 2016-73338 A | 5/2016 |
| WO | 2016/208239 A1 | 12/2016 |
| WO | 2017/203958 A1 | 11/2017 |

* cited by examiner

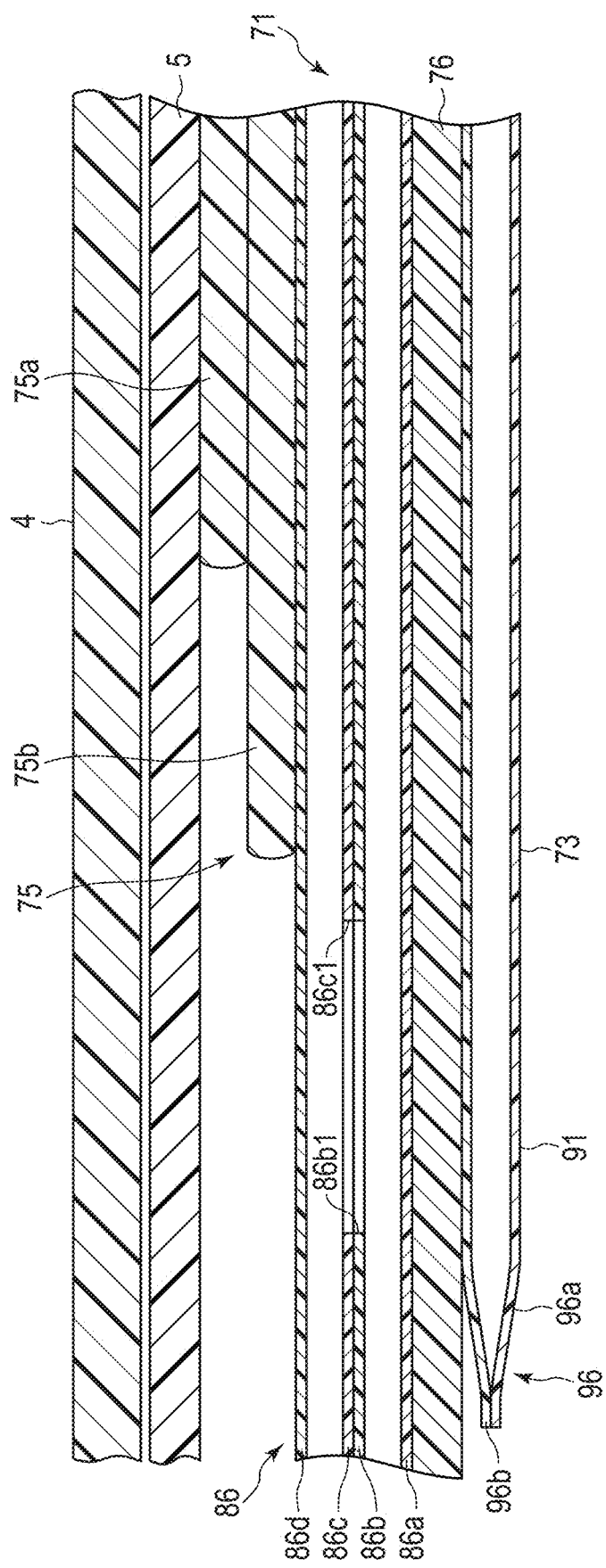
F I G. 12

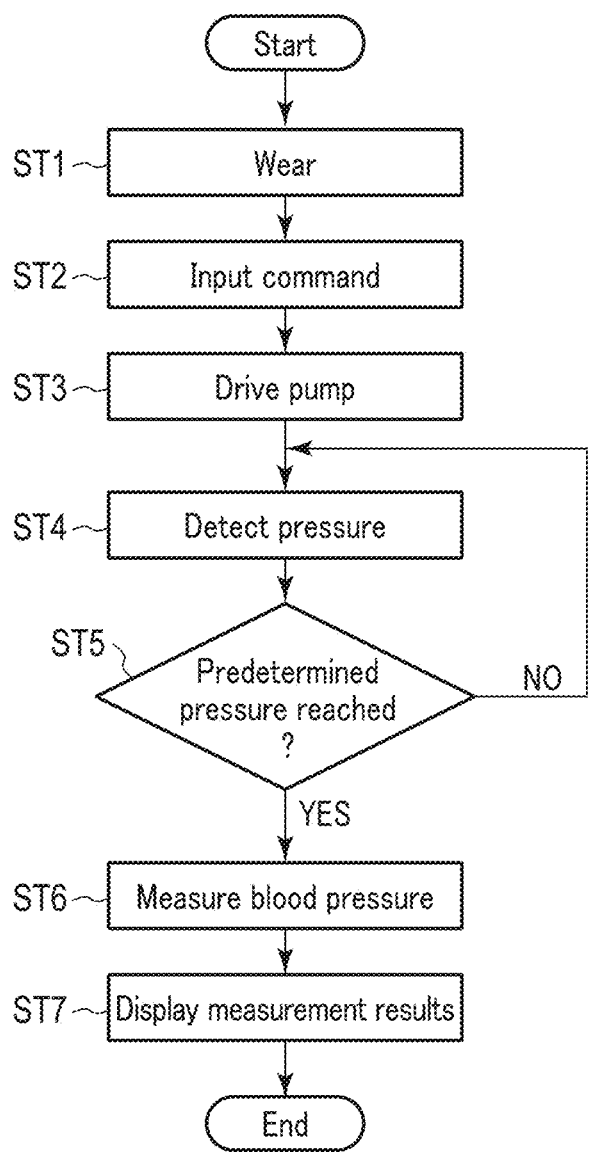
F I G. 16

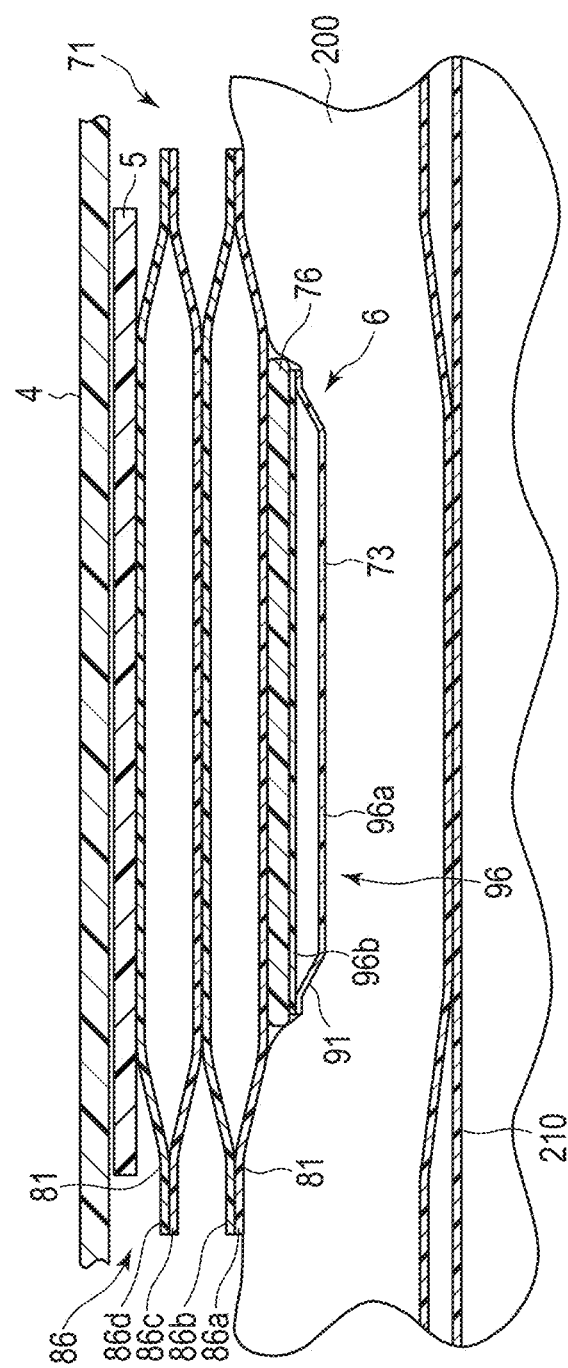
F I G. 22

BLOOD PRESSURE MEASURING DEVICE

CROSS-REFERENCE TO RELATED APPLICATIONS

This is a Continuation Application of PCT application No. PCT/JP2018/046234, filed Dec. 17, 2018, which was published under PCT Article 21(2) in Japanese.

This application is based upon and claims the benefit of priority from Japanese Patent Application No. 2017-253065, filed Dec. 28, 2017, the entire contents of which are incorporated herein by reference.

BACKGROUND

Field

The present invention relates to a blood pressure measuring device for the measurement of blood pressure.

Description of the Related Art

In recent years, a blood pressure measuring device for the use of blood pressure measurement has been utilized not only in medical facilities but also in households as a means to confirm health condition. A blood pressure measuring device measures blood pressure by detecting vibrations of an arterial wall, by, for example, wrapping a sensing cuff around an upper arm, a wrist, or the like of a living body, inflating and deflating the sensing cuff, and detecting the pressure of the sensing cuff with the use of a pressure sensor.

For example, a so-called "integrated-type blood pressure measuring device", in which a cuff and a device main body that supplies a fluid to the cuff are integrally formed, is known as the above-described blood pressure measuring device. In recent years, such an integrated-type blood pressure measuring device has faced requirements to be downsized to a wearable device that can be worn on a wrist. Therefore, the cuff used in the blood pressure measuring device has also faced downsizing requirements.

Such a blood pressure measuring device has a drawback in that the accuracy of the results of blood pressure measurement decreases when wrinkles, folds, or the like are generated in the cuff whose pressure is to be detected using a pressure sensor. FIG. 23 shows an example of a cross-sectional image in which a blood pressure measuring device is worn on a wrist and a cuff is inflated. In the example shown in FIG. 23, when the blood pressure measuring device is worn on the wrist, wrinkles and folds are generated in the cuff so as to form a deep groove, and may divide the inner space of the cuff, as indicated by a portion X. In particular, as the cuff becomes smaller due to the downsizing of the blood pressure measuring device, the accuracy of the results of measurement of blood pressure may decrease.

A wearable device does not only pose problems when used for blood pressure measurement. It also poses problems when used, for example, as a biological information measuring device for the measurement of a pulse, etc., in that it cannot accurately measure a pulse. Accordingly, a technique in which an air cushion is provided to each of a first and second strap, in order to adjust a force of pulling a main body portion when the straps are wound around a measurement site, is known as a biological information measuring device capable of accurately measuring biological information such as a pulse, as disclosed in Jpn. Pat. Appln. KOKAI Publication No. 2016-073338. Jpn. Pat. Appln. KOKAI Publication No. 2016-073338 discloses a technique for a biological information measuring device in which a pressure detector is provided in a range of a main body portion, where each force by which each strap pulls the main body portion affects the main body portion, a CPU adjusts the pulling force of each strap by an adjustment amount based on each pressure detected by the pressure detector and a relationship between the two pressures, and detection of a biological signal is commenced after the adjustment.

SUMMARY

The biological information measuring device disclosed in Jpn. Pat. Appln. KOKAI Publication No. 2016-073338 is configured to detect biological information such as a pulse by receiving, at a light receiver, a reflection light reflected from a measurement target among the lights emitted from a light emitter. Therefore, the biological information measuring device is allowed to adjust the pulling force of each strap by adjusting the air cushion provided to each strap.

In the blood pressure measuring device, however, when the cuff is brought into close contact with a wrist by adjusting the pulling force of each strap, the cuff is partially pressed against the wrist, the device main body, and the like, and wrinkles or folds are likely to be generated in the cuff.

There are two arteries in the wrist, and a tendon between them; therefore, in the case of measuring blood pressure by compressing the region of the wrist where the arteries are present using the cuff, the pressure distribution of the tissues around the arteries varies when the region is compressed by the cuff. If the pressure distribution varies, correct pressure cannot be measured, and the extent of error in measurement results may increase.

As such, a technique that can suppress the generation of wrinkles, folds, and the like in a cuff is required of a blood pressure measuring device that measures blood pressure at a wrist.

According to one aspect, there is provided a blood pressure measuring device including: a device main body; a curler configured to bend along a circumferential direction of a wrist of a living body, including one end and another end separated from each other, also configured to come into contact with a portion of the wrist at least between a dorsal side and a palmar side, and further configured to be fixed to the device main body; a strap provided to the device main body, configured to cover an outer surface of the curler, and further configured to be mounted on the wrist; a sensing cuff arranged in a region of the wrist where arteries exist; a rubber plate provided on a side of the sensing cuff nearer to the curler and configured to elastically deform; a pressing cuff provided between the curler and the rubber plate and configured to press the sensing cuff; and a cuff provided on a side of the curler nearer to the living body and arranged on the dorsal side of the wrist.

In this aspect, the "portion of the wrist at least between a dorsal side and a palmar side" refers to a region which is on a lateral side of the wrist between the dorsal side and the palmar side, and is located in a direction perpendicular to the direction of gravity when the arm is extended forward with the back of the hand facing upward and the palm of the hand facing downward. Furthermore, the "portion of the wrist at least between a dorsal side and a palmar side" means a region of the wrist located on an outer side of the radius and the ulna in the direction in which the radius and the ulna are aligned. Also, the region of the wrist where arteries exist includes a region on the palmar side of the wrist where exists the tendon approximately in the center, and covers two arteries adjacent to the tendon in the circumferential direction of the wrist.

The pressing cuff, the sensing cuff and the cuff are wrapped around the wrist when blood pressure is measured, and are inflated when a fluid is supplied thereto. Also, the pressing cuff, the sensing cuff and the cuff of this aspect include a bag-shaped structure such as an air bag.

According to this aspect, when the cuff is inflated in a state where the holder is in contact with the portion of the wrist between the dorsal side and the palmar side, the skin of the wrist in the region touched by the holder is pulled by the cuff together with at least one of the strap or the curler. Since the skin of the wrist on the palmar side is pulled thereby, sagging of the skin of the wrist on the palmar side, and the like are reduced, and the sensing cuff comes into close contact on its surface. As a result, it is not only possible to reduce variations in the pressure distribution of the region compressed by the sensing cuff that occur when the wrist is compressed, but also to suppress the generation of wrinkles and folds in the sensing cuff.

Also, according to this aspect, the blood pressure measuring device is configured so that, as the pressing cuff presses the rubber plate and the sensing cuff by pressing the curler, the rubber plate and the sensing cuff bend in accordance with the shape of the curler, thereby preventing the sensing cuff from being wrinkled or folded. Furthermore, according to this aspect, since the pressing cuff presses the curler, the palmar side of the wrist can be compressed in a manner that is less likely to cause wrinkles and folds in the sensing cuff.

Also, according to this aspect, an elastically deformable rubber plate is provided between the curler and the sensing cuff, and is in close contact with the curler and the sensing cuff. Therefore, a gap between the curler and the wrist is filled, allowing the wrist and the sensing cuff to be in close contact with each other.

There is provided the blood pressure measuring device according to the above aspect, further including a flat plate provided between the curler and the pressing cuff and arranged in a region of the wrist where a tendon exists.

According to this aspect, the flat plate between the curler and the rubber plate can press all three of the tendon of the wrist, the pressing cuff and the sensing cuff in the region where the tendon exists. Therefore, as the sensing cuff is pressed by the tendon, the generation of wrinkles and folds in the sensing cuff can be suppressed.

There is provided the blood pressure measuring device according to the above aspect, wherein the thickness of the cuff in a direction of inflating from the curler toward the wrist is larger than those of the pressing cuff and the sensing cuff.

According to this aspect, the strap and the curler deform in a direction in which the strap and the curler come into contact with the wrist by making the thickness of the cuff in the inflating direction be larger than those of the pressing cuff and the sensing cuff. Therefore, the strap and the curler come into close contact with the portion of the wrist between the dorsal side and the palmar side, and the skin of the wrist between the dorsal side and the palmar side is pulled. Thus, the skin of the wrist on the palmar side facing the sensing cuff is stretched, and the strap and the curler on the palmar side are pulled. As a result, the sensing cuff is in suitably close contact with the surface of the wrist on the palmar side, making it possible to further suppress the generation of wrinkles and folds in the sensing cuff.

The present invention can provide a blood pressure measuring device capable of suppressing the generation of wrinkles and folds in a sensing cuff.

BRIEF DESCRIPTION OF THE DRAWINGS

FIG. 12 is a cross-sectional view of configurations of a strap, the curler, and the cuff structure of the blood pressure measuring device.

FIG. 16 is a flowchart showing an example of the use of the blood pressure measuring device.

FIG. 22 is a cross-sectional diagram schematically showing a configuration of the blood pressure measuring device in which the blood pressure measuring device is worn on a wrist and the cuff structure is inflated.

DETAILED DESCRIPTION

First Embodiment

Hereinafter, an example of a blood pressure measuring device 1 according to a first embodiment of the present invention will be described with reference to FIGS. 1 to 15.

Figure 1:
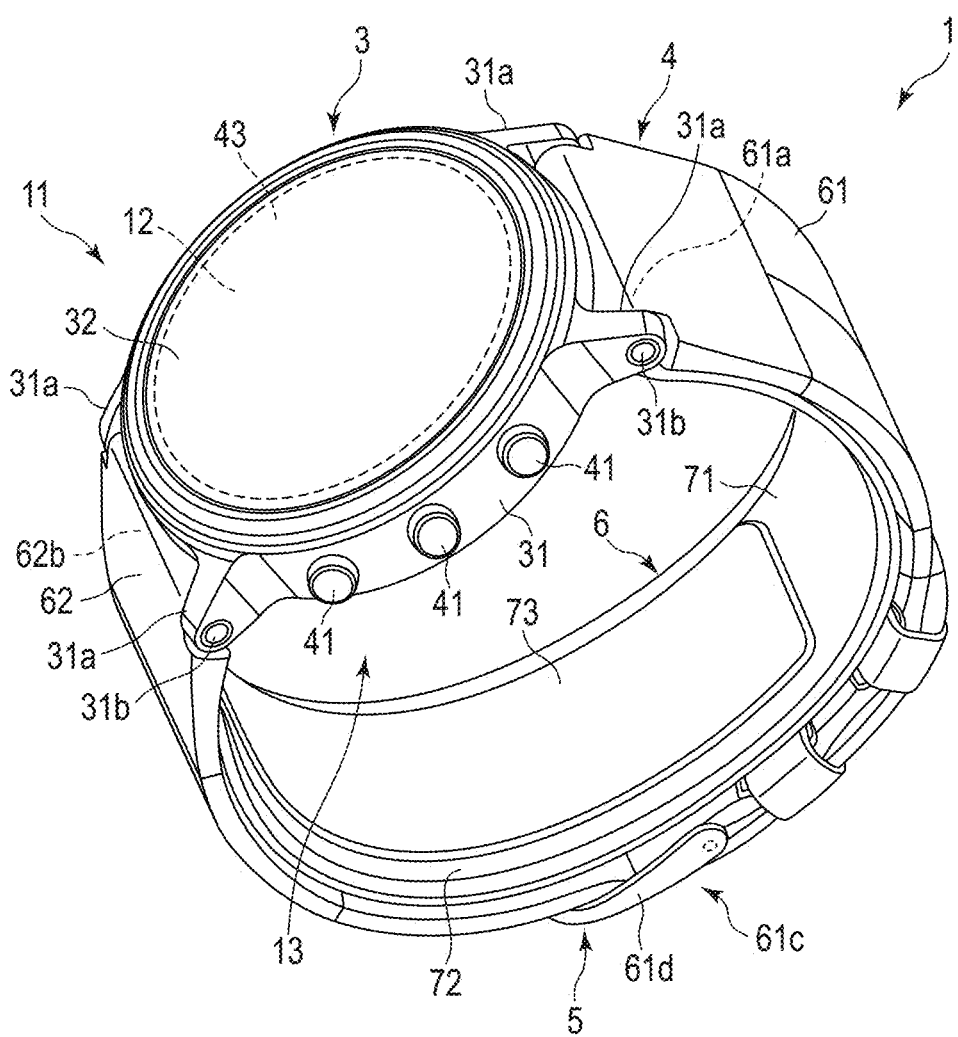
FIG. 1 is a perspective view of a configuration of a blood pressure measuring device according to a first embodiment of the present invention.
Figure 2:
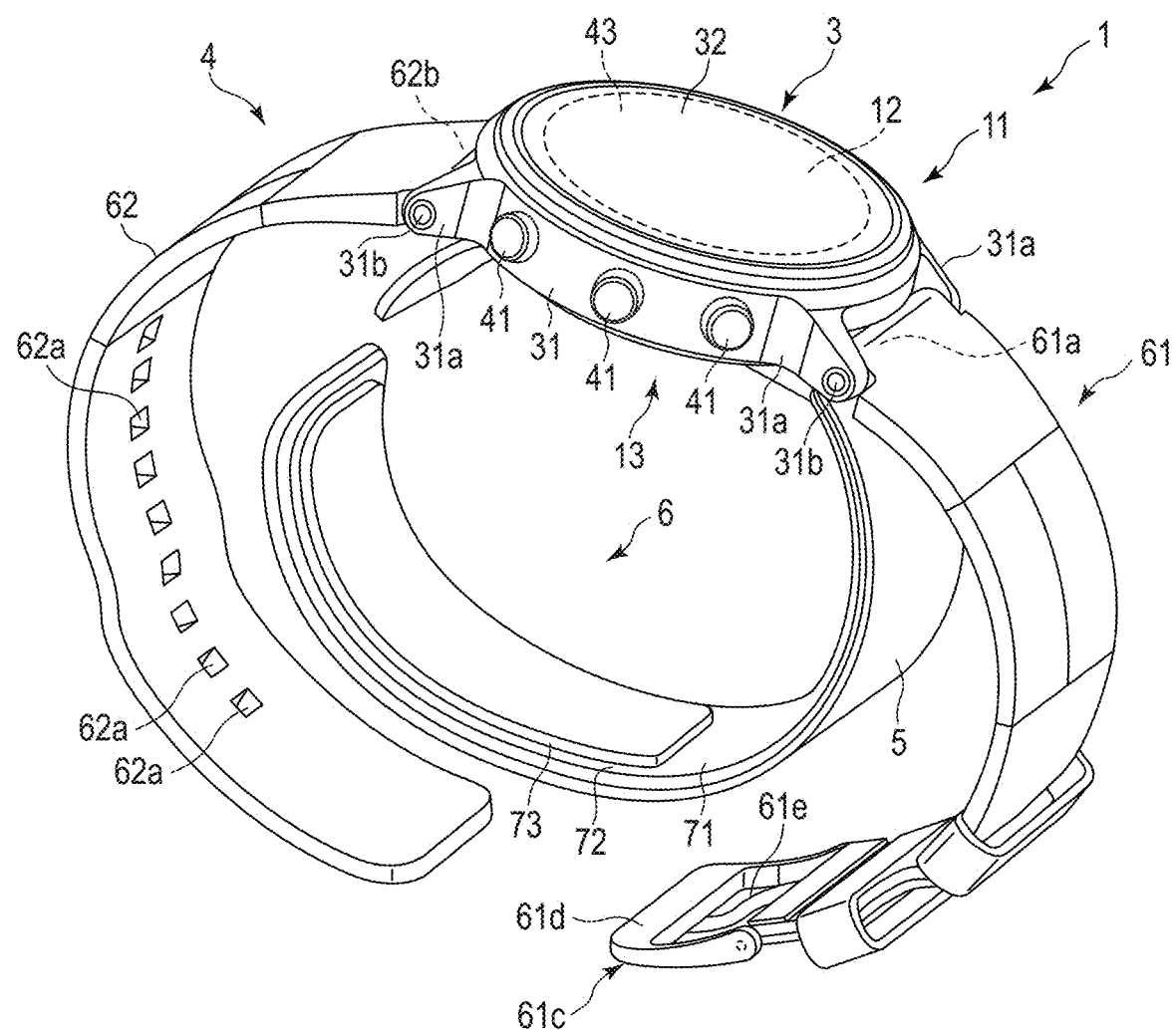
FIG. 2 is a perspective view of a configuration of the blood pressure measuring device.
Figure 3:
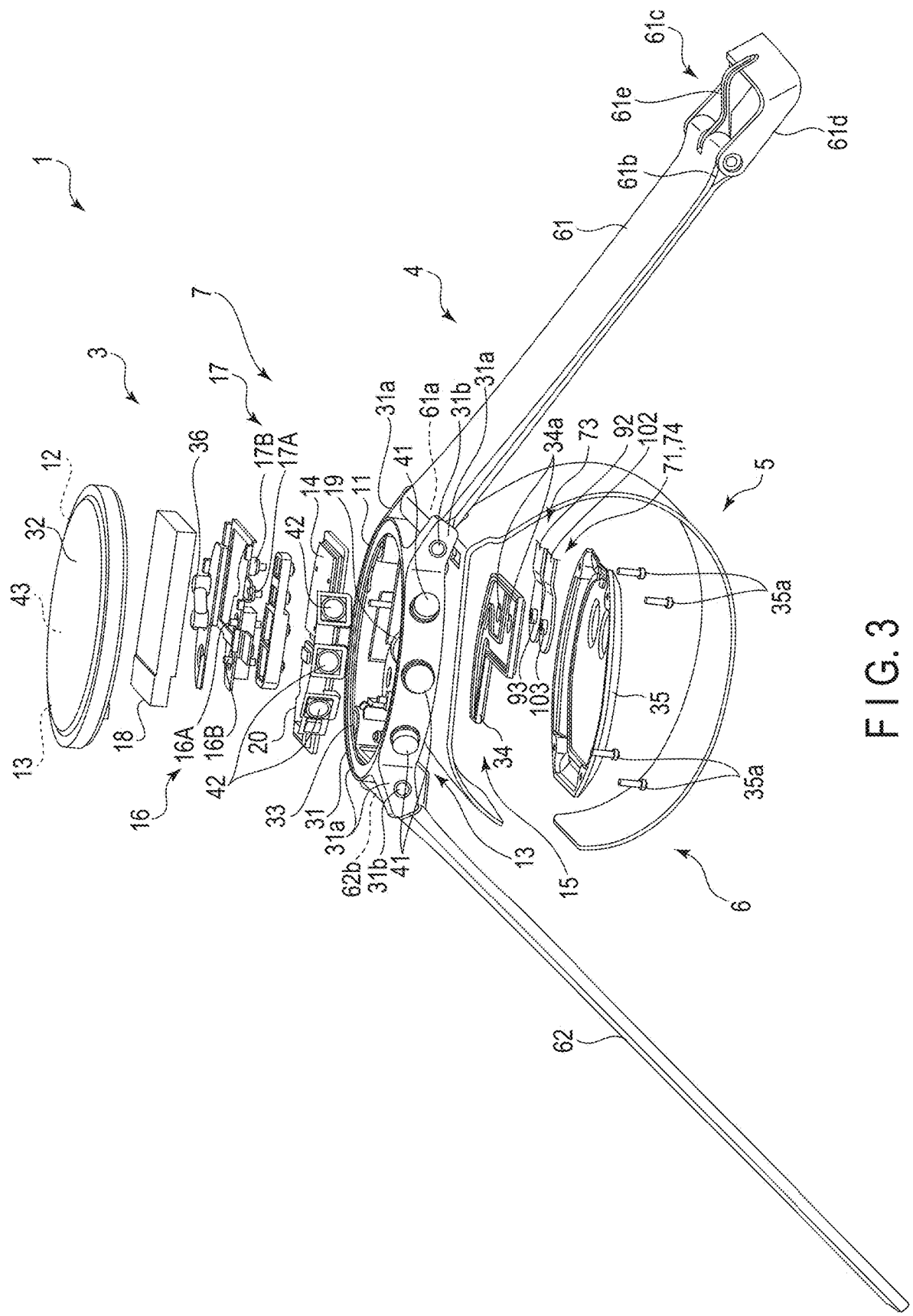
FIG. 3 is an exploded view of a configuration of the blood pressure measuring device.
Figure 4:
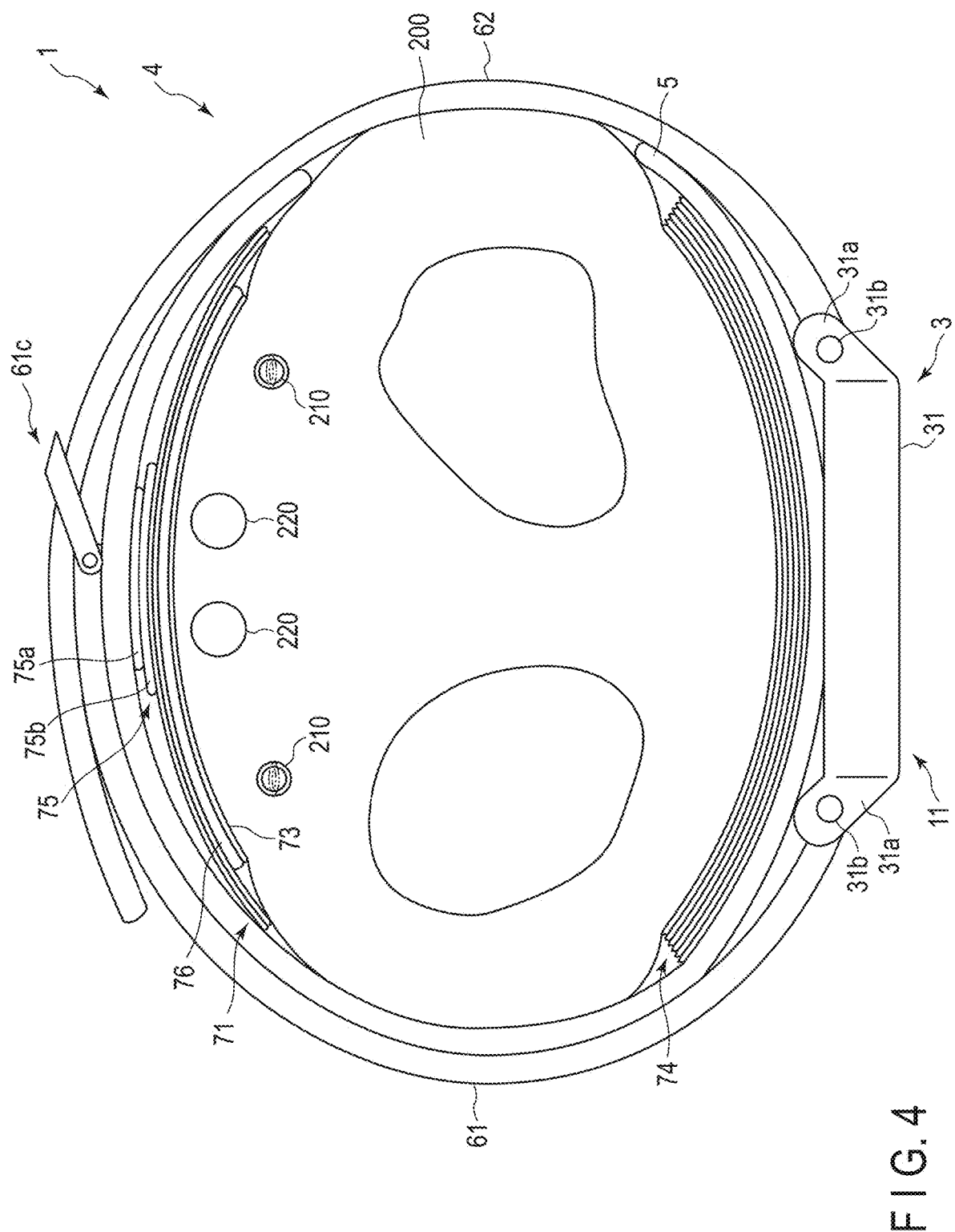
FIG. 4 is an explanatory diagram showing a state in which the blood pressure measuring device is worn on a wrist.
Figure 5:
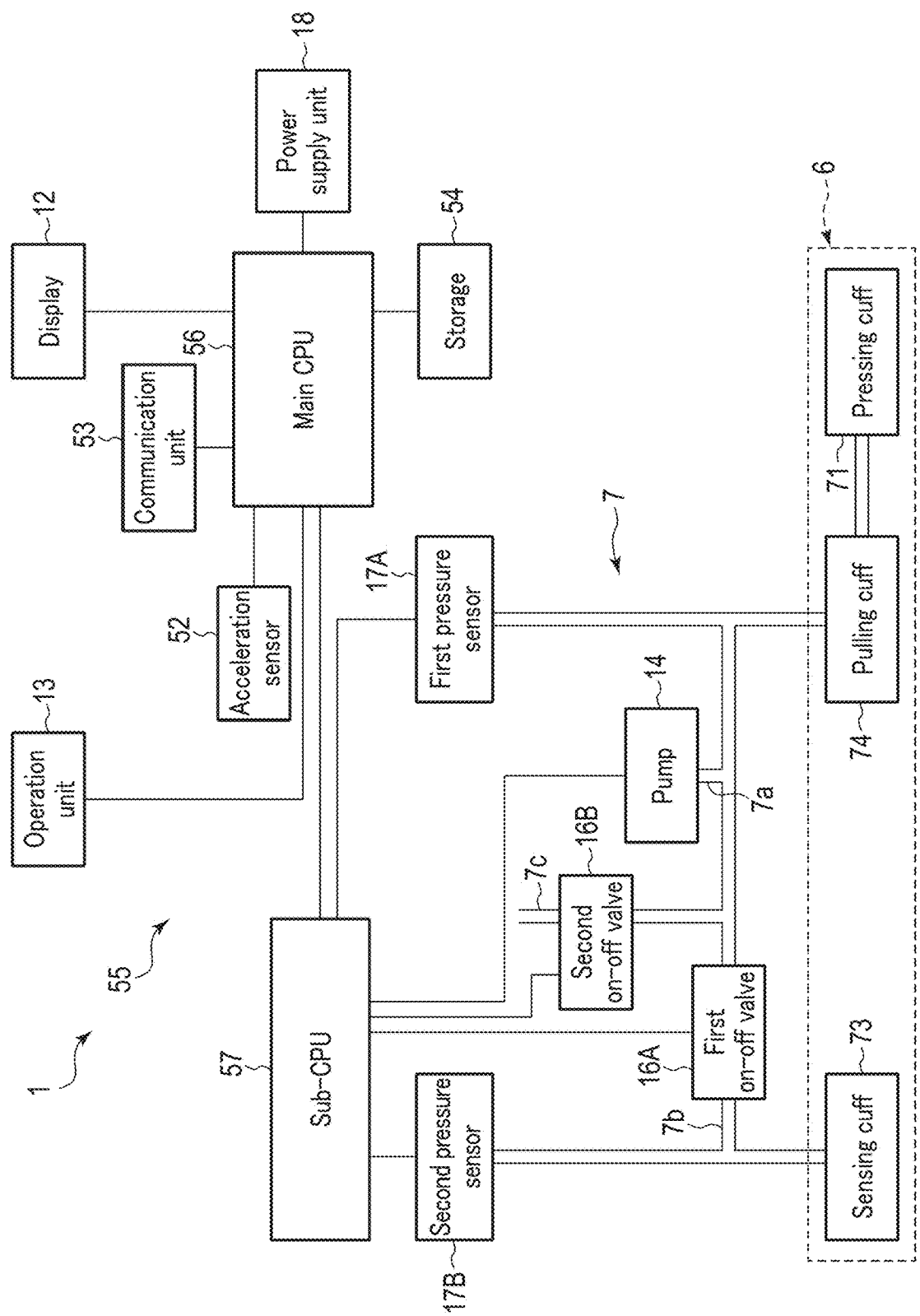
FIG. 5 is a block diagram showing a configuration of the blood pressure measuring device.
Figure 6:
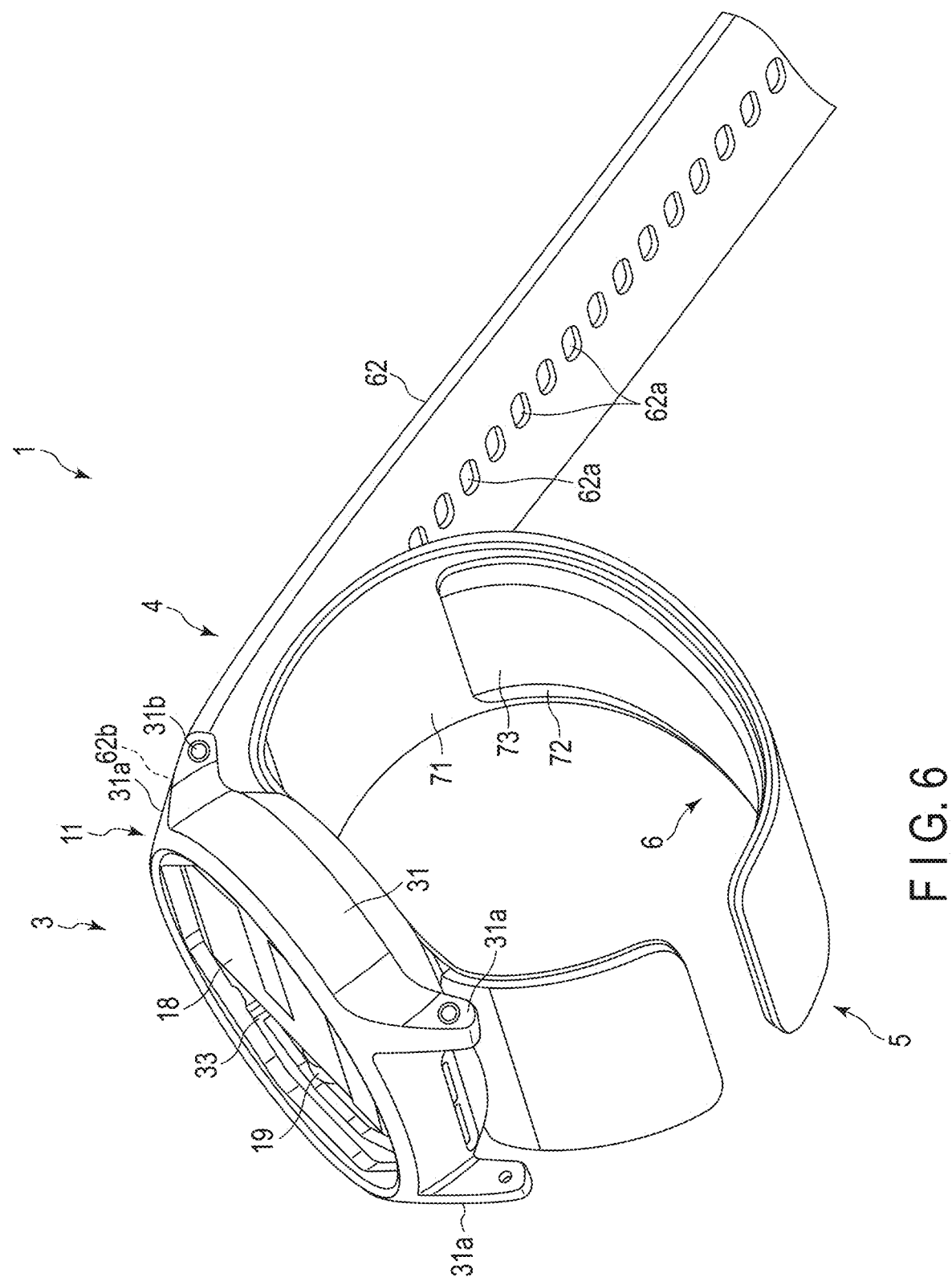
FIG. 6 is a perspective view of a configuration of a device main body and a curler of the blood pressure measuring device.
Figure 7:
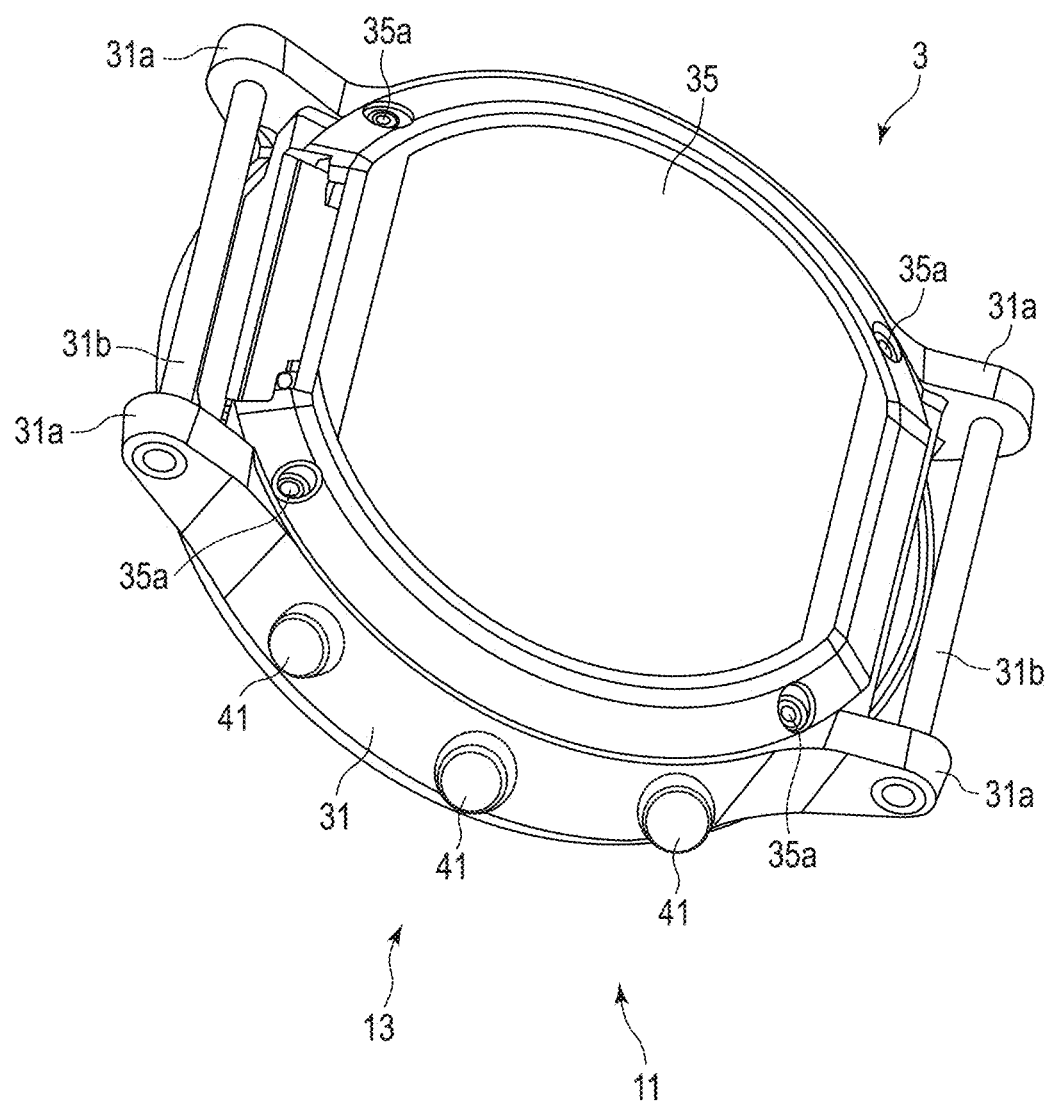
FIG. 7 is a perspective view of a configuration of the device main body of the blood pressure measuring device.
Figure 8:
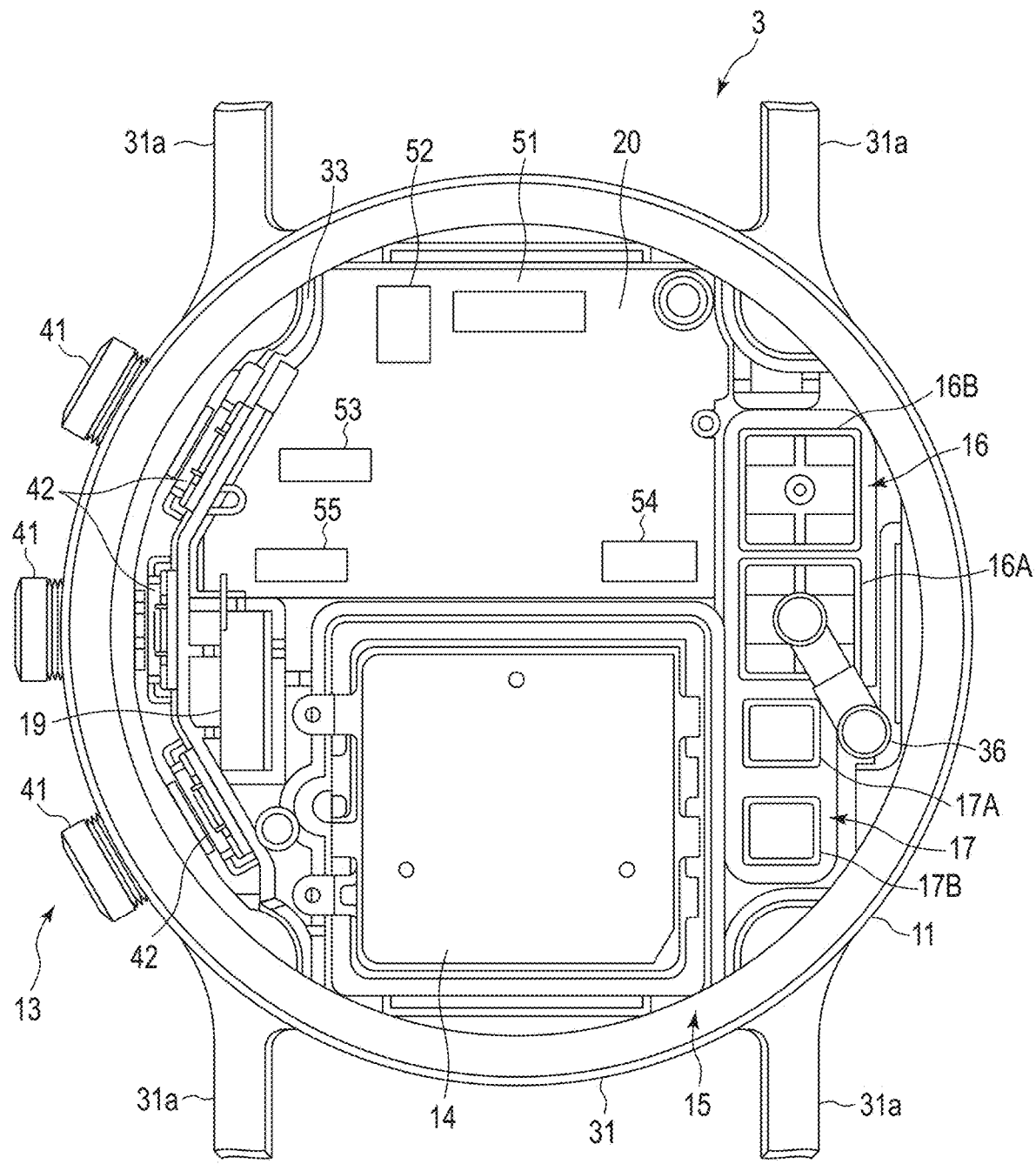
FIG. 8 is a plan view of an internal configuration of the device main body.
Figure 9:
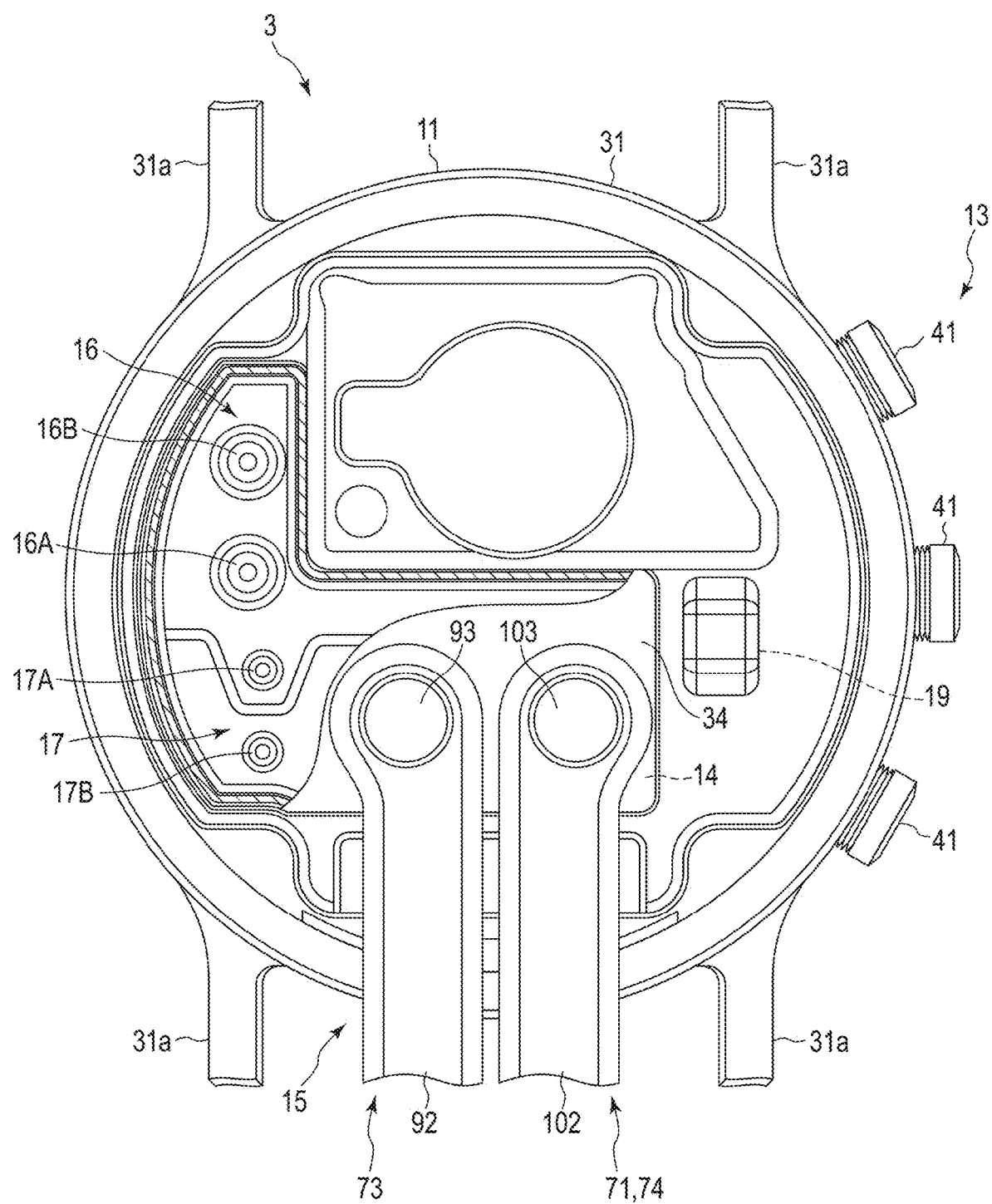
FIG. 9 is a plan view of an internal configuration of the device main body.
Figure 10:
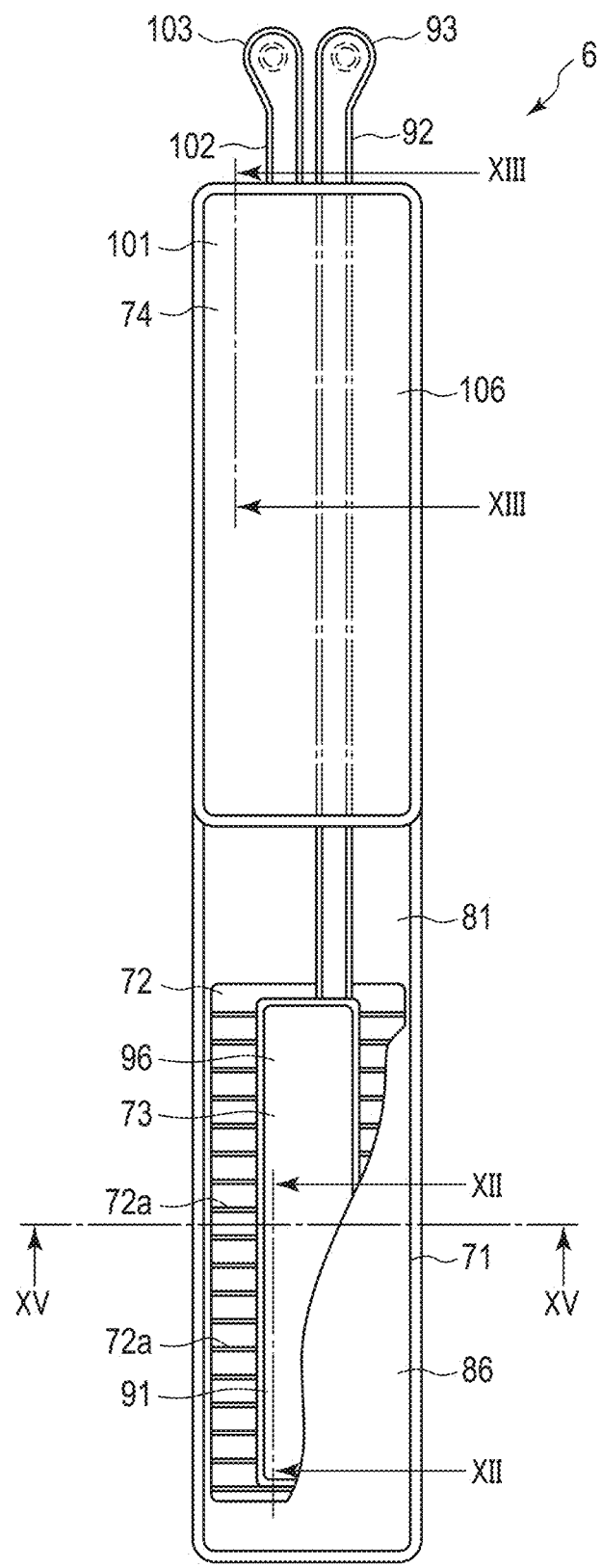
FIG. 10 is a plan view of a configuration of a cuff structure of the blood pressure measuring device.
Figure 11:
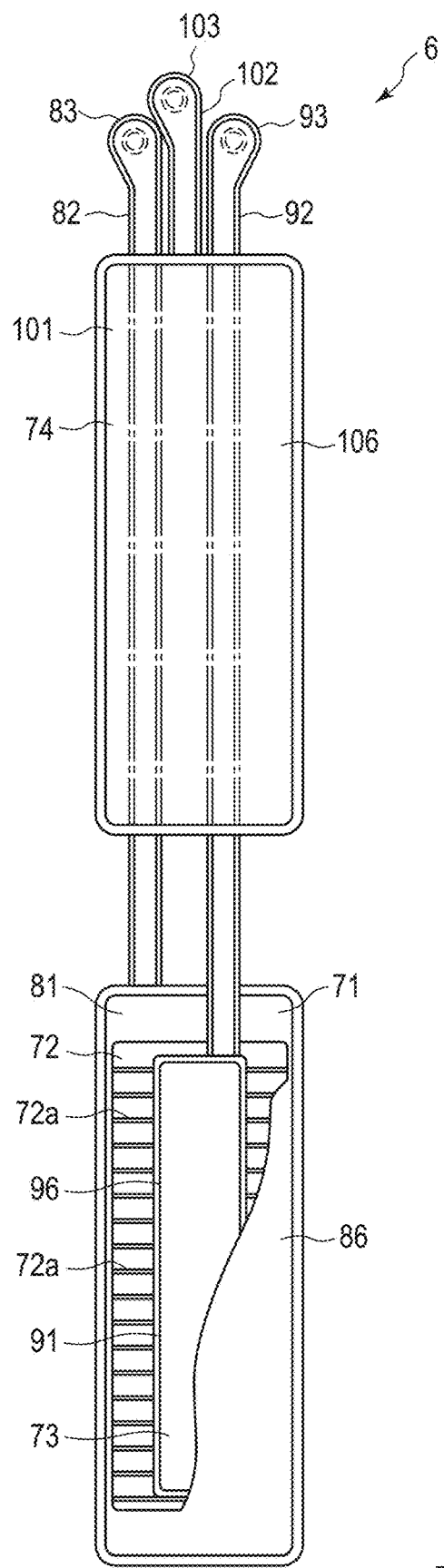
FIG. 11 is a plan view of another configuration of the cuff structure of the blood pressure measuring device.

FIG. 1 is a perspective view of a configuration of the blood pressure measuring device 1 according to the first embodiment of the present invention with a strap 4 closed. FIG. 2 is a perspective view of a configuration of the blood pressure measuring device 1 with the strap 4 opened. FIG. 3 is an exploded view of a configuration of the blood pressure measuring device 1. FIG. 4 is an explanatory diagram showing a state in which the blood pressure measuring device 1 is worn on a wrist. FIG. 5 is a block diagram showing a configuration of the blood pressure measuring device 1. FIG. 6 is a perspective view of configurations of a device main body 3 and a curler 5 of the blood pressure measuring device 1. FIG. 7 is a perspective view of a configuration of the device main body 3 of the blood pressure measuring device 1, as viewed from a back cover 35 side. FIGS. 8 and 9 are plan views of an internal configuration of the device main body 3, as viewed from a windshield 32 side and the back cover 35 side, respectively. FIG. 10 is a plan view of a configuration of a cuff structure 6 of the blood pressure measuring device 1, as viewed from a sensing cuff 73 side. FIG. 11 is a plan view of another configuration example of the cuff structure 6, as viewed from the sensing cuff 73 side.

Figure 13:
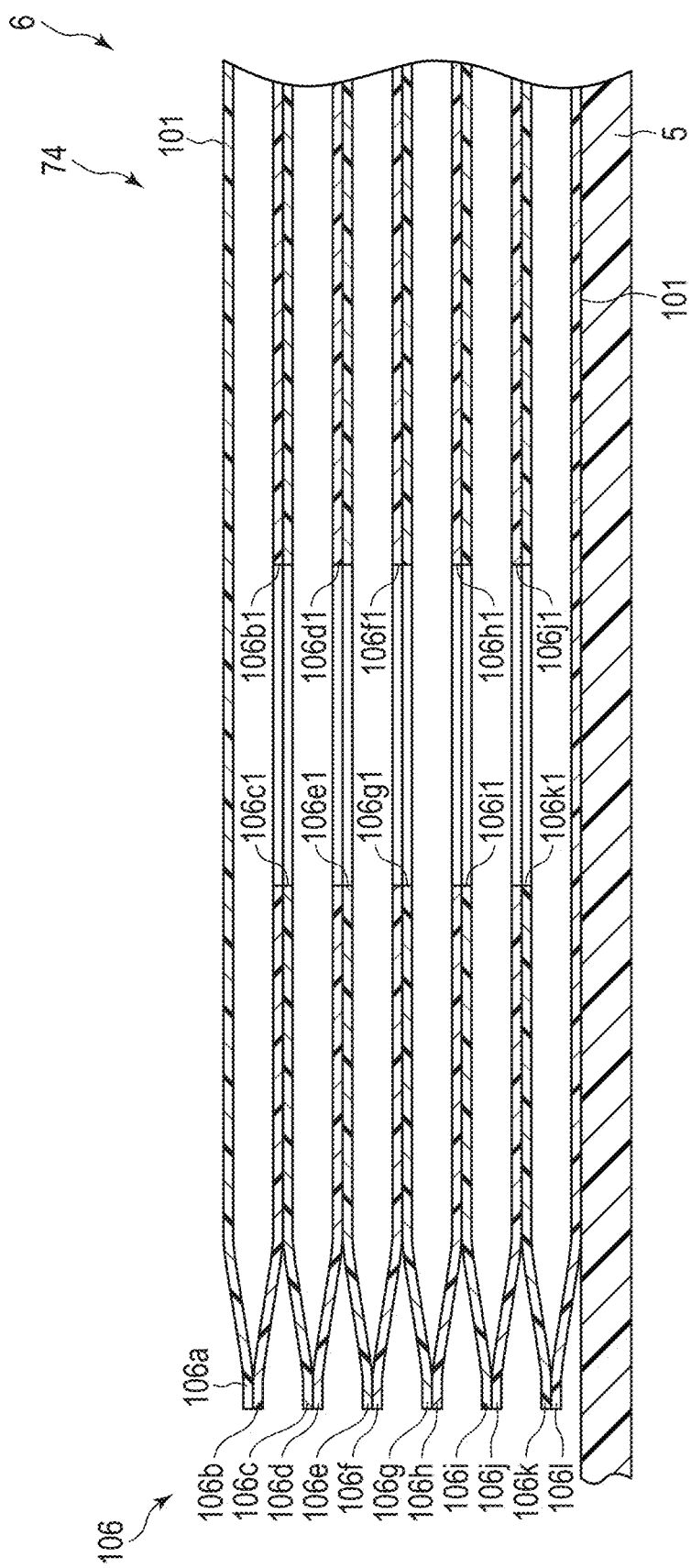
FIG. 13 is a cross-sectional view of configurations of the curler and the cuff structure of the blood pressure measuring device.
Figure 14:
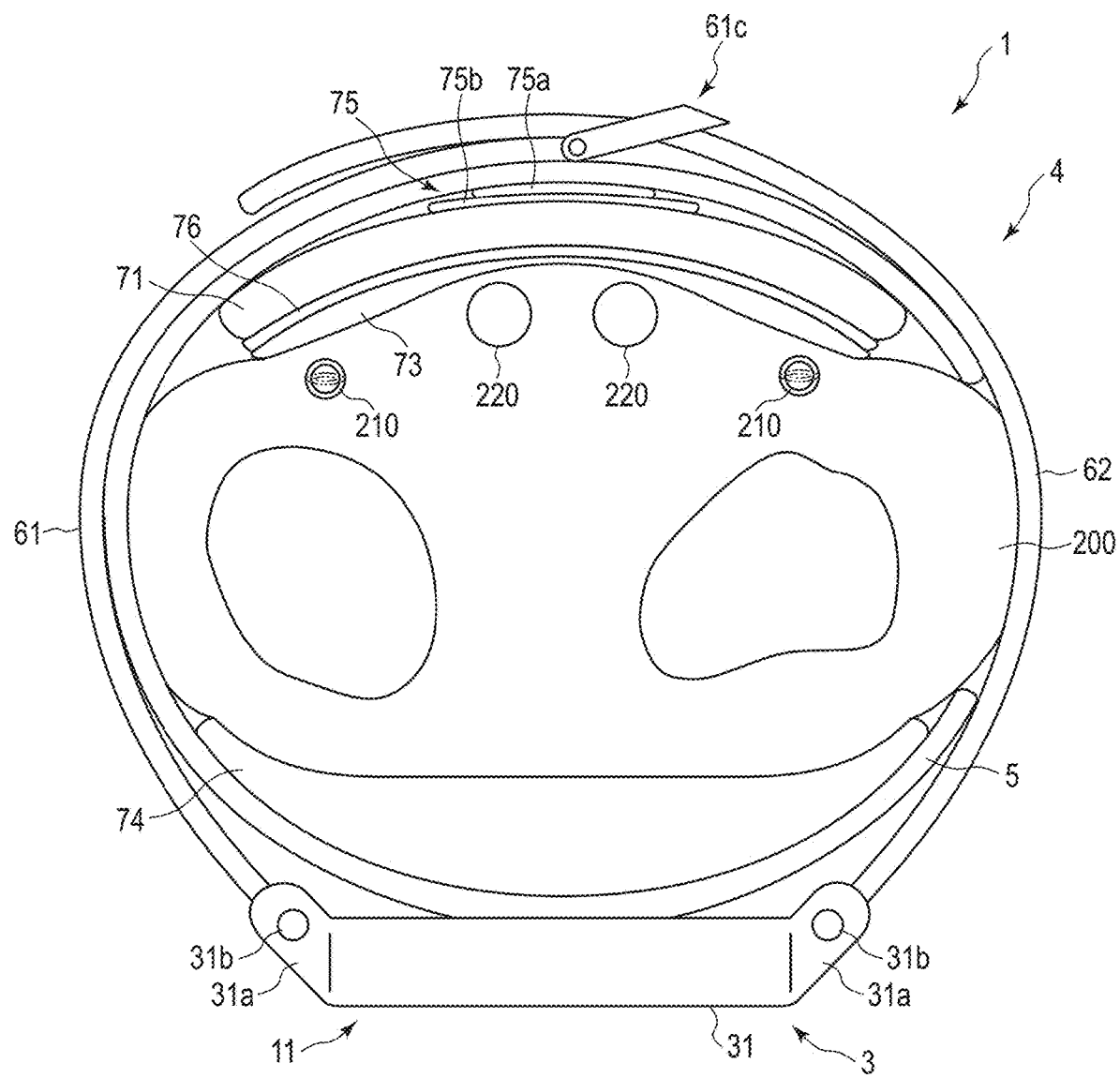
FIG. 14 is an explanatory diagram showing a configuration of the blood pressure measuring device in which the blood pressure measuring device is worn on a wrist and the cuff structure is inflated.
Figure 15:
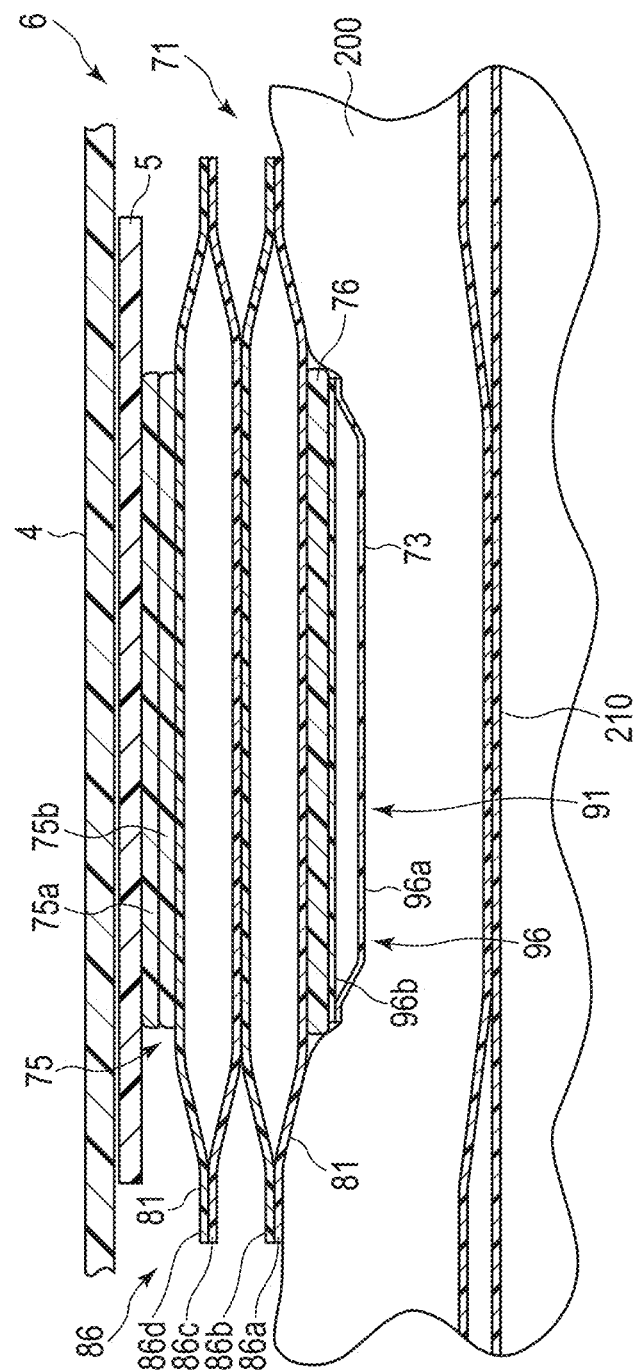
FIG. 15 is a cross-sectional diagram schematically showing a configuration of the blood pressure measuring device in which the blood pressure measuring device is worn on a wrist and the cuff structure is inflated.

FIG. 12 is a cross-sectional diagram schematically showing configurations of the strap 4, the curler 5, and the cuff structure 6 of the blood pressure measuring device 1 taken along line XII-XII in FIG. 10. FIG. 13 is a cross-sectional diagram schematically showing configurations of the curler 5 and the cuff structure 6 of the blood pressure measuring device 1 taken along line XIII-XIII in FIG. 10. FIGS. 14 and 15 are explanatory diagrams respectively showing a configuration of the blood pressure measuring device 1, in which the blood pressure measuring device 1 is worn on a wrist and the cuff structure 6 is inflated to measure blood pressure. FIG. 15 is a cross-sectional view of a configuration of the blood pressure measuring device 1 when measuring blood pressure, taken along line XV-XV in FIG. 10. In FIG. 12, the strap 4, the curler 5, and the cuff structure 6 are schematically shown in a linear shape for convenience of explanation; however, these components are in a bent shape when provided in the blood pressure measuring device 1.

The blood pressure measuring device 1 is an electronic blood pressure measuring device that is worn on a living body. In the present embodiment, an electronic blood pressure measuring device in the form of a wearable device worn on a wrist 200 of a living body will be described. As shown in FIGS. 1 to 13, the blood pressure measuring device 1 includes: the device main body 3; the strap 4; the curler 5; the cuff structure 6 with a pressing cuff 71, a sensing cuff 73, and a pulling cuff 74 that is fluidly continuous with the pressing cuff 71; and a fluid circuit 7. In the present embodiment, the pulling cuff 74 is an example of the "cuff" of the present invention.

As shown in FIGS. 1 to 13, the device main body 3 includes a case 11, a display 12, an operation unit 13, a pump 14, a flow passage section 15, an on-off valve 16, a pressure sensor 17, a power supply unit 18, a vibration motor 19, and a control substrate 20. The device main body 3 is a supply device that supplies a fluid to the pressing cuff 71 by using the pump 14, the on-off valve 16, the pressure sensor 17, the control substrate 20, and the like. The case 11 includes an outer case 31; a windshield 32 that covers an upper opening of the outer case 31; a base 33 provided in a lower part of the inside of the outer case 31; a flow passage cover 34 that covers a part of a back surface of the base 33; and a back cover 35 that covers a lower side of the outer case 31. The case 11 also includes a flow passage tube 36 constituting a part of the fluid circuit 7.

The outer case 31 is formed in a cylindrical shape. The outer case 31 includes: pairs of lugs 31a provided at symmetrical positions in the circumferential direction of the outer peripheral surface; and spring rods 31b respectively provided between the paired lugs 31a. The windshield 32 is a circular glass plate.

The base 33 holds the display 12, the operation unit 13, the pump 14, the on-off valve 16, the pressure sensor 17, the power supply unit 18, the vibration motor 19, and the control substrate 20. The base 33 forms a part of the flow passage section 15.

The flow passage cover 34 is fixed to a back surface of the base 33, which is an outer surface of the base 33 on the back cover 35 side. A groove is provided in one or both of the base 33 and the flow passage cover 34, thereby forming a part of the flow passage section 15.

The back cover 35 covers an end of the outer case 31 on the living body side. The back cover 35 is fixed to an end of the outer case 31 or the base 33 on the living body side by, for example, four screws 35a or the like.

The flow passage tube 36 forms a part of the flow passage section 15. The flow passage tube 36 connects, for example, the on-off valve 16 and a part of the base 33 constituting the flow passage section 15.

The display 12 is disposed on the base 33 of the outer case 31 and directly below the windshield 32. The display 12 is electrically connected to the control substrate 20. The display 12 is, for example, a liquid crystal display or an organic electroluminescence display. The display 12 displays various kinds of information including date and time, and measurement results of blood pressure values, such as systolic blood pressure and diastolic blood pressure, a heart rate, and the like.

The operation unit 13 is configured to allow a user to input a command. For example, the operation unit 13 includes: a plurality of buttons 41 provided to the case 11; a sensor 42 that detects an operation of the buttons 41; and a touch panel 43 provided to the display 12 or the windshield 32. The operation unit 13 is operated by a user to convert a command into an electric signal. The sensor 42 and the touch panel 43 are electrically connected to the control substrate 20 and output an electric signal to the control substrate 20.

For example, three buttons 41 are provided. The buttons 41 are supported by the base 33 and protrude from the outer peripheral surface of the outer case 31. The plurality of buttons 41 and the plurality of sensors 42 are supported by the base 33. For example, the touch panel 43 is provided integrally to the windshield 32.

The pump 14 is, for example, a piezoelectric pump. The pump 14 compresses the air and supplies the compressed air to the cuff structure 6 via the flow passage section 15. The pump 14 is electrically connected to the controller 55.

The flow passage section 15 is an air flow passage formed of a groove or the like provided in the flow passage cover 34 that covers the back cover 35 side of the base 33 and the main surface of the base 33 on the back cover 35 side. The flow passage section 15 forms a flow passage leading from the pump 14 to the pressing cuff 71 and the pulling cuff 74, and a flow passage leading from the pump 14 to the sensing cuff 73. The flow passage section 15 also forms a flow passage leading from the pressing cuff 71 and the pulling cuff 74 to the atmosphere, and a flow passage leading from the sensing cuff 73 to the atmosphere. The flow passage cover 34 includes a connected portion 34a to which the pressing cuff 71 and the sensing cuff 73 or the pulling cuff 74 and the sensing cuff 73 are connected. The connected portion 34a is, for example, a cylindrical nozzle provided to the flow passage cover 34.

The on-off valve 16 opens and closes a part of the flow passage section 15. For example, a plurality of on-off valves 16 are provided, and selectively open and close the flow passage leading from the pump 14 to the pressing cuff 71 and the pulling cuff 74; the flow passage leading from the pump 14 to the sensing cuff 73; the flow passage leading from the pressing cuff 71 and the pulling cuff 74 to the atmosphere; and the flow passage leading from the sensing cuff 73 to the atmosphere, depending on the combination of the opening and closing of the on-off valves 16. For example, two on-off valves 16 are used.

The pressure sensor 17 detects the pressure of the pressing cuff 71, the sensing cuff 73, and the pulling cuff 74. The pressure sensor 17 is electrically connected to the control substrate 20. The pressure sensor 17 is electrically connected to the control substrate 20, converts the detected pressure into an electric signal, and outputs the electric signal to the control substrate 20. For example, the pressure sensor 17 is provided in the flow passage leading from the pump 14 to the pressing cuff 71 and the pulling cuff 74, and the flow passage leading from the pump 14 to the sensing cuff 73. Since these flow passages are continuous with the pressing cuff 71, the sensing cuff 73, and the pulling cuff 74, the pressures in these flow passages become the pressures in the internal spaces of the pressing cuff 71, the sensing cuff 73, and the pulling cuff 74.

The power supply unit 18 is, for example, a secondary battery such as a lithium ion battery. The power supply unit 18 is electrically connected to the control substrate 20. The power supply unit 18 supplies power to the control substrate 20.

As shown in FIGS. 5 and 8, the control substrate 20 includes, for example, a substrate 51, an acceleration sensor 52, a communication unit 53, a storage 54, and a controller 55. The control substrate 20 is configured by mounting the acceleration sensor 52, the communication unit 53, the storage 54, and the controller 55 on the substrate 51.

The substrate 51 is fixed to the base 33 of the case 11 by a screw or the like.

The acceleration sensor 52 is, for example, a three-axis acceleration sensor. The acceleration sensor 52 outputs, to the controller 55, acceleration signals representing accelerations of the device main body 3 in three directions that are orthogonal to one another. For example, the acceleration sensor 52 is used to measure the amount of activity of the living body wearing the blood pressure measuring device 1 based on the detected accelerations.

The communication unit 53 is configured to be able to transmit and receive information to and from an external device in a wireless or wired manner. For example, the communication unit 53 transmits information controlled by the controller 55 and information such as measured blood pressure values, pulse, and the like to an external device via a network, and receives a program for software update, etc., from the external device via the network to transmit the program, etc., to the controller.

In the present embodiment, the network is, for example, the Internet, but is not limited thereto. The network may be a network such as a local area network (LAN) provided in a hospital, or direct communication with an external device using, for example, a cable having a terminal of a predetermined standard such as a USB may be adopted. Therefore, the communication unit 53 may include a plurality of wireless antennas, micro USB connectors, and the like.

The storage 54 stores in advance program data for controlling the entire blood pressure measuring device 1 and the fluid circuit 7, setting data for the setting of various functions of the blood pressure measuring device 1, calculation data for the calculation of blood pressure values and a pulse from a pressure measured by the pressure sensor 17, and the like. The storage 54 also stores information such as measured blood pressure values and pulse.

The controller 55 is formed of one or more CPUs, and controls the operation of the entire blood pressure measuring device 1 and the operation of the fluid circuit 7. The controller 55 is electrically connected to the display 12, the operation unit 13, the pump 14, the on-off valves 16, and the pressure sensors 17, and supplies electric power. Also, the controller 55 controls the operations of the display 12, the pump 14, and the on-off valves 16 based on the electric signals output from the operation unit 13 and the pressure sensor 17.

For example, the controller 55 includes a main CPU 56 that controls the operation of the entire blood pressure measuring device 1 and a sub-PU 57 that controls the operation of the fluid circuit 7, as shown in FIG. 5. For example, when a command to measure blood pressure is input from the operation unit 13, the sub-PU 57 drives the pump 14 and the on-off valves 16 to send compressed air to the pressing cuff 71 and the sensing cuff 73.

The sub-PU 57 also controls the driving and stoppage of the pump 14 and the opening and closing of the on-off valves 16 based on the electric signal output from the pressure sensor 17, selectively sends compressed air to the pressing cuff 71 and the sensing cuff 73, and selectively depressurizes the pressing cuff 71 and the sensing cuff 73. The main CPU 56 obtains measurement results of blood pressure values, such as systolic blood pressure and diastolic blood pressure, a heart rate, and the like from the electric signal output from the pressure sensor 17, and outputs an image signal corresponding to the measurement results to the display 12.

As shown in FIGS. 1 to 3, the strap 4 includes a first strap 61 provided to one of the pairs of lugs 31a and the spring rod 31b, and a second strap 62 provided to the other pair of lugs 31a and the spring rod 31b. The strap 4 is wrapped around the wrist 200 via the curler 5.

The first strap 61 is a so-called "parent" and is formed in a band shape. The first strap 61 includes a first hole 61a provided at one end and perpendicular to the longitudinal direction of the first strap 61, a second hole 61b provided at the other end and perpendicular to the longitudinal direction of the first strap 61, and a buckle 61c provided in the second hole 61b. The first hole 61a has an inner diameter so that the spring rod 31b can be inserted thereinto and the first strap 61 can rotate with respect to the spring rod 31b. That is, the first hole 61a is disposed between the paired lugs 31a and at the spring rod 31b, so that the first strap 61 is rotatably held by the outer case 31.

The second hole 61b is provided at a distal end of the first strap 61. The buckle 61c includes a rectangular frame-shaped body 61d and a prodding stick 61e rotatably attached to the frame-shaped body 61*d*. One side of the frame-shaped body 61*d* to which the prodding stick 61*e* is attached is inserted into the second hole 61*b*, so that the frame-shaped body 61*d* is rotatably attached with respect to the first strap 61.

The second strap 62 is a so-called "pointed end", and formed in a band shape having a width that allows the second strap 62 to be inserted into the frame-shaped body 61*d*. The second strap 62 includes a plurality of small holes 62*a* into which the prodding stick 61*e* is inserted. The second strap 62 also includes a third hole 62*b* provided at one end of the second strap 62 and perpendicular to the longitudinal direction of the second strap 62. The third hole 62*b* has an inner diameter so that the spring rod 31*b* can be inserted thereinto and that the second strap 62 can rotate with respect to the spring rod 31*b*. That is, the third hole 62*b* is disposed between the paired lugs 31*a* and at the spring rod 31*b*, so that the second strap 62 is rotatably held by the outer case 31.

The strap 4 described above forms an annular shape along the circumferential direction of the wrist 200 together with the outer case 31 as the second strap 62 is inserted into the frame-shaped body 61*d* and the prodding stick 61*e* is inserted into the small hole 62*a*, thereby integrally connecting the first strap 61 and the second strap 62 to each other.

The curler 5 is made of a resin material. The curler 5 is formed in a band shape bent along the circumferential direction of the wrist. For example, one end and the other end of the curler 5 are separated from each other, and an outer surface of the curler 5 on the side of one end is fixed to the back cover 35 of the device main body 3. One end of the curler 5 protrudes from the device main body 3, and one end and the other end of the curler 5 are adjacent to each other.

As a specific example, the curler 5 has a shape bent along the circumferential direction of the wrist 200, for example, in a side view from a direction perpendicular to the circumferential direction of the wrist, in other words, the longitudinal direction of the wrist, as shown in FIGS. 1 to 3 and FIG. 6. For example, the curler 5 extends from the device main body 3 to the palmar side of the wrist 200 through the dorsal side of the wrist 200 and one side of the wrist 200, and extends to the other side of the wrist 200. That is, the curler 5 bends along the circumferential direction of the wrist and thereby extends over most parts of the wrist 200 in the circumferential direction of the wrist 200, and both ends of the curler 5 are separated from each other by a predetermined interval.

The curler 5 has a hardness encompassing both flexibility and shape-retaining capability. The "flexibility" means that the curler 5 deforms in the radial direction when an external force is applied to the curler 5, and means that when the curler 5 is pressed by the strap 4, for example, the curler 5 deforms so as to approach the wrist, conform to the shape of the wrist, or trace the shape of the wrist, as viewed from a side of the curler 5. The "shape-retaining capability" means that the curler 5 can maintain a pre-formed shape when no external force is applied thereto; and in the present embodiment, it means that the curler 5 can maintain a shape bent along the circumferential direction of the wrist. The curler 5 is made of a resin material. For example, the curler 5 is made of polypropylene and has a thickness of about 1 mm. The curler 5 holds the cuff structure 6 along the inner surface shape of the curler 5.

As shown in FIGS. 1 to 4 and 10 to 15, the cuff structure 6 includes the pressing cuff 71, the sensing cuff 73, the pulling cuff 74, the flat plate 75, and a rubber plate 76. The cuff structure 6 is fixed to the curler 5. The cuff structure 6 is configured so that the pressing cuff 71, the sensing cuff 73, the flat plate 75, and the rubber plate 76 are stacked on the curler 5, and that the pulling cuff 74 is disposed on the curler 5 so as to be separated from the pressing cuff 71, the sensing cuff 73, the flat plate 75, and the rubber plate 76.

As a specific example, the cuff structure 6 is configured so that the pressing cuff 71, the sensing cuff 73, the pulling cuff 74, the flat plate 75, and the rubber plate 76 are disposed on the inner surface of the curler 5. The cuff structure 6 is configured so that the flat plate 75, the pressing cuff 71, the rubber plate 76, and the sensing cuff 73 are stacked on the inner surface of the curler 5 on the palmar side of the wrist 200 in the mentioned order from the inner surface of the curler 5 toward the living body side, to be fixed. Also, the cuff structure 6 is configured so that the pulling cuff 74 is disposed on the inner surface of the curler 5 on the dorsal side of the wrist 200. Each member of the cuff structure 6 is fixed to a member adjacent thereto by a double-sided tape, an adhesive, or the like.

The pressing cuff 71 is fluidly connected to the pump 14 via the flow passage section 15. The pressing cuff 71 is inflated to press the rubber plate 76 and the sensing cuff 73 toward the living body. The pressing cuff 71 includes a plurality of, for example, two layers of air bags 81.

The air bag 81 is a bag-shaped structure. Since the blood pressure measuring device 1 is configured to use the air with the pump 14 in the present embodiment, an air bag will be described. However, when a fluid other than the air is used, the bag-shaped structure may be a fluid bag such as a liquid bag. The plurality of air bags 81 are stacked and fluidly communicate with each other in the stacking direction.

The two layers of air bags 81 are formed in a rectangular shape elongated in one direction. The air bag 81 is formed by, for example, combining two sheet members 86 elongated in one direction and welding the edges thereof by heat. As a specific example, the two layers of air bags 81 include, from the living body side: a first sheet member 86*a*; a second sheet member 86*b* forming the first layer of air bag 81 with the first sheet member 86*a*; a third sheet member 86*c* integrally bonded to the second sheet member 86*b*; and a fourth sheet member 86*d* forming the second layer of air bag 81 with the third sheet member 86*c*, as shown in FIGS. 10 to 12.

The first sheet member 86*a* and the second sheet member 86*b* form the air bag 81 by the welding of the peripheral edges of the four sides of the sheet members. The second sheet member 86*b* and the third sheet member 86*c* are disposed to face each other, and each include a plurality of openings 86*b*1 and 86*c*1 that fluidly connect the two air bags 81. The fourth sheet member 86*d* has an adhesive layer or a double-sided tape on the outer surface thereof on the flat plate 75 side, and is attached to the flat plate 75 by the adhesive layer or the double-sided tape.

The third sheet member 86*c* and the fourth sheet member 86*d* form the air bag 81 by the welding of the peripheral edges of the four sides of the sheet members.

The sensing cuff 73 is fixed to the main surface of the rubber plate 76 on the living body side. As shown in FIG. 14, the sensing cuff 73 directly contacts the region of the wrist 200 where arteries 210 exist. The arteries 210 are a radial artery and an ulnar artery. The sensing cuff 73 is formed in the same shape as that of the rubber plate 76 or in a shape smaller than that of the rubber plate 76, in the longitudinal direction and the width direction of the rubber plate 76. The sensing cuff 73 is inflated to compress a region of the wrist 200 on the palmar side where the arteries 210 exist. The sensing cuff 73 is pressed toward the living body by the inflated pressing cuff 71 via the rubber plate 76.

As a specific example, the sensing cuff 73 includes one air bag 91, a tube 92 communicating with the air bag 91, and a connector 93 provided at a distal end of the tube 92. The sensing cuff 73 is configured so that one of the main surfaces of the air bag 91 is fixed to the rubber plate 76. For example, the sensing cuff 73 is attached to the main surface of the rubber plate 76 on the living body side by a double-sided tape, an adhesive layer, or the like.

The air bag 91 is a bag-shaped structure. Since the blood pressure measuring device 1 is configured to use the air with the pump 14 in the present embodiment, an air bag will be described. However, when a fluid other than the air is used, the bag-shaped structure may be a liquid bag or the like. A plurality of air bags 91 described above are stacked and fluidly communicate with each other in the stacking direction.

The air bag 91 is formed in a rectangular shape elongated in one direction. The air bag 91 is formed by, for example, combining two sheet members elongated in one direction and the welding of the edges thereof by heat. As a specific example, the air bag 91 includes a fifth sheet member 96a and a sixth sheet member 96b from the living body side, as shown in FIGS. 10 and 12.

For example, the fifth sheet member 96a and the sixth sheet member 96b are configured so that the tube 92 fluidly continuous with the internal space of the air bag 91 is disposed on one side of the fifth sheet member 96a and the sixth sheet member 96b, and is fixed by welding. For example, the fifth sheet member 96a and the sixth sheet member 96b form the air bag 91 by the welding of the peripheral edges of the four sides of the sheet members with the tube 92 disposed between the fifth sheet member 96a and the sixth sheet member 96b, thereby integrally welding the tube 92 thereto.

The tube 92 is provided at one end in the longitudinal direction of the air bag 91. As a specific example, the tube 92 is provided at an end of the air bag 91 close to the device main body 3. The tube 92 includes a connector 93 at its distal end. The tube 92 forms a flow passage between the device main body 3 and the air bag 91 in the fluid circuit 7. The connector 93 is connected to the connected portion 34a of the flow passage cover 34. The connector 93 is, for example, a nipple.

The pulling cuff 74 is an example of the cuff. The pulling cuff 74 is fluidly connected to the pump 14 via the flow passage section 15. The pulling cuff 74 is inflated to press the curler 5 with respect to the wrist 200 away from the wrist 200, thereby pulling the strap 4 and the curler 5 toward the dorsal side of the wrist 200. The pulling cuff 74 includes a plurality of, for example, six layers of air bags 101, a tube 102 communicating with the air bags 101, and a connector 103 provided at a distal end of the tube 102.

The pulling cuff 74 is configured so that in the inflation direction, that is, in the direction in which the curler 5 and the wrist 200 face each other in the present embodiment, the thickness of the pulling cuff 74 at the time of inflation is larger than the thickness of the pressing cuff 71 in the inflation direction at the time of inflation and the thickness of the sensing cuff 73 in the inflation direction at the time of inflation. That is, the air bag 101 of the pulling cuff 74 has a layer structure larger in the number of layers than the air bag 81 of the pressing cuff 71 and the air bag 91 of the sensing cuff 73, and the thickness of the pulling cuff 74 when inflated from the curler 5 toward the wrist 200 is larger than those of the pressing cuff 71 and the sensing cuff 73.

The air bag 101 is a bag-shaped structure. Since the blood pressure measuring device 1 is configured to use the air with the pump 14 in the present embodiment, an air bag will be described. However, when a fluid other than the air is used, the bag-shaped structure may be a fluid bag such as a liquid bag. The plurality of air bags 101 are stacked and fluidly communicate with each other in the stacking direction.

The six layers of air bags 101 are formed in a rectangular shape elongated in one direction. The air bag 101 is formed by, for example, combining two sheet members 106 elongated in one direction and welding the edges thereof by heat. As a specific example, the six layers of air bags 101 include, from the living body side: a seventh sheet member 106a; an eighth sheet member 106b; a ninth sheet member 106c; a tenth sheet member 106d; an eleventh sheet member 106e; a twelfth sheet member 106f; a thirteenth sheet member 106g; a fourteenth sheet member 106h; a fifteenth sheet member 106i; a sixteenth sheet member 106j; a seventeenth sheet member 106k; and an eighteenth sheet member 106l, as shown in FIG. 13. The six layers of air bags 101 are integrally formed by bonding the respective sheet members 106 by a double-sided tape, an adhesive, welding, or the like.

The seventh sheet member 106a and the eighth sheet member 106b form the first layer of air bag 101 by the welding of the peripheral edges of the four sides of the sheet members. The eighth sheet member 106b and the ninth sheet member 106c are disposed to face each other and integrally bonded. The eighth sheet member 106b and the ninth sheet member 106c include a plurality of openings 106b1 and 106c1 that fluidly connect adjacent air bags 101. The ninth sheet member 106c and the tenth sheet member 106d form the second layer of air bag 101 by the welding of the peripheral edges of the four sides of the sheet members.

The tenth sheet member 106d and the eleventh sheet member 106e are disposed to face each other and integrally bonded. The tenth sheet member 106d and the eleventh sheet member 106e include a plurality of openings 106d1 and 106e1 that fluidly connect adjacent air bags 101. The eleventh sheet member 106e and the twelfth sheet member 106f form the third layer of air bag 101 by the welding of the peripheral edges of the four sides of the sheet members.

The twelfth sheet member 106f and the thirteenth sheet member 106g are disposed to face each other and integrally bonded. The twelfth sheet member 106f and the thirteenth sheet member 106g include a plurality of openings 106f1 and 106g1 that fluidly connect adjacent air bags 101. The thirteenth sheet member 106g and the fourteenth sheet member 106h form the fourth layer of air bag 101 by the welding of the peripheral edges of the four sides of the sheet members.

The fourteenth sheet member 106h and the fifteenth sheet member 106i are disposed to face each other and integrally bonded. The fourteenth sheet member 106h and the fifteenth sheet member 106i include a plurality of openings 106h1 and 106i1 that fluidly connect adjacent air bags 101. The fifteenth sheet member 106i and the sixteenth sheet member 106j form the fifth layer of air bag 101 by the welding of the peripheral edges of the four sides of the sheet members.

The sixteenth sheet member 106j and the seventeenth sheet member 106k are disposed to face each other and integrally bonded. The sixteenth sheet member 106j and the seventeenth sheet member 106k include a plurality of openings 106j1 and 106k1 that fluidly connect adjacent air bags 101. The seventeenth sheet member 106k and the eighteenth sheet member 106l form the sixth layer of air bag 101 by the welding of the peripheral edges of the sheet members to form a rectangular frame shape. Also, for example, the tube 102 fluidly continuous with the internal space of the air bag 101 is disposed on one side of the seventeenth sheet member 106k and the eighteenth sheet member 106l, and is fixed by welding. For example, the seventeenth sheet member 106k and the eighteenth sheet member 106l form the air bag 101 by welding the peripheral edges of the sheet members to form a rectangular frame shape, with the tube 102 disposed between the seventeenth sheet member 106k and the eighteenth sheet member 106l, thereby integrally welding the tube 102 thereto.

For example, the sixth layer of air bag 101 is integrally formed with the second layer of air bag 81 of the pressing cuff 71. That is, the seventeenth sheet member 106k is integrally formed with the third sheet member 86c, and the eighteenth sheet member 106l is integrally formed with the fourth sheet member 86d.

More specifically, the third sheet member 86c and the seventeenth sheet member 106k form a rectangular sheet member elongated in one direction, and the eighteenth sheet member 106l and the fourth sheet member 86d form a rectangular sheet member elongated in one direction. These sheet members are overlapped with each other. One end side is welded in a manner to form a rectangular frame shape without welding a part of the side on the other end side, thereby forming the second layer of air bag 81 of the pressing cuff 71; and the other end side is welded in a manner to form a rectangular frame shape without welding a part of the side on one end side, thereby forming the sixth layer of air bag 101 of the pulling cuff 74. Since a part of the sides of the second layer of air bag 81 and the sixth layer of air bag 101 opposed to each other is not welded, the second layer of air bag 81 and the sixth layer of air bag 101 are fluidly continuous with each other.

The tube 102 is connected to one of the six layers of air bags 101, and is provided at one end in the longitudinal direction of the air bag 101. As a specific example, the tube 102 is provided at an end on the curler 5 side of the six layers of air bags 101 and close to the device main body 3. The tube 102 includes a connector 103 at its distal end. The tube 102 forms a flow passage between the device main body 3 and the air bag 101 in the fluid circuit 7. The connector 103 is connected to the connected portion 34a of the flow passage cover 34. The connector 103 is, for example, a nipple.

In the present embodiment, the configuration has been described in which a part of the pulling cuff 74 is integrally formed with the pressing cuff 71 so that the pulling cuff 74 is fluidly continuous with the pressing cuff 71; however, the present invention is not limited thereto. For example, the pulling cuff 74 may be formed separately from the pressing cuff 71 and be fluidly discontinuous with the pressing cuff 71, as shown in FIG. 11. In such a configuration, the pulling cuff 74 may be further provided with a tube 82 and a connector 83 in a manner similar to the pressing cuff 71 and the sensing cuff 73, and a flow passage for supplying a fluid to the pulling cuff 74, a check valve, and a pressure sensor may be connected in the fluid circuit 7.

The sheet members 86, 96, and 106 forming the pressing cuff 71, the sensing cuff 73, and the pulling cuff 74 are made of a thermoplastic elastomer. For example, thermoplastic polyurethane resin (hereinafter referred to as "TPU"), vinyl chloride resin, ethylene-vinyl acetate resin, thermoplastic polystyrene resin, thermoplastic polyolefin resin, thermoplastic polyester resin, and thermoplastic polyamide resin may be used as the thermoplastic elastomer forming the sheet members 86, 96, and 106. TPU is preferably used as the thermoplastic elastomer. The sheet member may have a single-layer structure or a multi-layer structure.

The sheet members 86, 96, and 106 are not limited to the thermoplastic elastomer, and may be a thermosetting elastomer such as silicone or a combination of a thermoplastic elastomer (for example, TPU) and a thermosetting elastomer (for example, silicone).

When a thermoplastic elastomer is used for the sheet members 86, 96, and 106, a molding method such as T-die extrusion molding or injection molding is adopted, and when a thermosetting elastomer is used for the sheet members 86, 96, and 106, a molding method such as mold casting molding is adopted. The sheet members are molded by the molding method and thereafter sized into a predetermined shape. Then, the sized pieces are bonded by adhesion, welding, or the like to form the bag-shaped structures 81, 91, and 101. As a bonding method, a high-frequency welder or laser welding is used when a thermoplastic elastomer is used, and a molecular adhesive is used when a thermosetting elastomer is used.

The flat plate 75 is provided so as to face a region of the wrist 200 where the tendon 220 exists, and is formed of a material having a hardness capable of indirectly pressing the tendon 220 via the sensing cuff 73 or the like. The flat plate 75 is formed of, for example, polypropylene. The flat plate 75 is fixed, by an adhesive, a double-sided tape, or the like, at a position on the inner surface of the curler 5 and facing the region of the wrist 200 where the tendon 220 exists. The flat plate 75 includes, for example, a first plate member 75a fixed to the curler 5 and a second plate member 75b fixed to the first plate member 75a and to which the fourth sheet member 86d is fixed.

The rubber plate 76 is made of a rubber material, has a thin plate shape, and is elastically deformable. The rubber plate 76 is attached to the outer surface of the first sheet member 86a of the pressing cuff 71 by an adhesive layer, a double-sided tape, or the like. The rubber plate 76 is formed in a plate shape having a thickness of about 1 mm. The rubber plate 76 is formed to have a length covering the palmar side of the wrist 200. The rubber plate 76 transmits the pressing force from the pressing cuff 71 to the main surface of the sensing cuff 73 on the rubber plate 76 side, in a state of conforming to the shape of the wrist 200.

The fluid circuit 7 is formed of the case 11, the pump 14, the flow passage section 15, the on-off valve 16, the pressure sensor 17, the pressing cuff 71, the sensing cuff 73, and the pulling cuff 74. Hereinafter, a specific example of the fluid circuit 7 will be described in which the two on-off valves 16 used in the fluid circuit 7 are referred to as a "first on-off valve 16A" and a "second on-off valve 16B", and the two pressure sensors 17 used in the fluid circuit 7 are referred to as a "first pressure sensor 17A" and a "second pressure sensor 17B".

As shown in FIG. 5, the fluid circuit 7 includes, for example, a first flow passage 7a which continues from the pump 14 to the pressing cuff 71 and the pulling cuff 74, a second flow passage 7b which is formed by branching a middle portion of the first flow passage 7a and continues from the pump 14 to the sensing cuff 73, and a third flow passage 7c which connects the first flow passage 7a and the atmosphere. The first flow passage 7a includes the first pressure sensor 17A. The first on-off valve 16A is provided between the first flow passage 7a and the second flow passage 7b. The second flow passage 7b includes the second pressure sensor 17B. The second on-off valve 16B is provided between the first flow passage 7a and the third flow passage 7c.

In the fluid circuit 7 described above, when the first on-off valve 16A and the second on-off valve 16B are closed, only the first flow passage 7a is connected to the pump 14, and the pump 14 and the pressing cuff 71 are fluidly connected. In the fluid circuit 7, when the first on-off valve 16A is opened and the second on-off valve 16B is closed, the first flow passage 7a and the second flow passage 7b are connected, and the pump 14 and the pulling cuff 74, the pulling cuff 74 and the pressing cuff 71, and the pump 14 and the sensing cuff 73 are fluidly connected. In the fluid circuit 7, when the first on-off valve 16A is closed and the second on-off valve 16B is closed, the first flow passage 7a and the third flow passage 7c are connected, and the pressing cuff 71, the pulling cuff 74, and the atmosphere are fluidly connected. In the fluid circuit 7, when the first on-off valve 16A and the second on-off valve 16B are opened, the first flow passage 7a, the second flow passage 7b, and the third flow passage 7c are connected, and the pressing cuff 71, the sensing cuff 73, the pulling cuff 74, and the atmosphere are fluidly connected.

Figure 17:
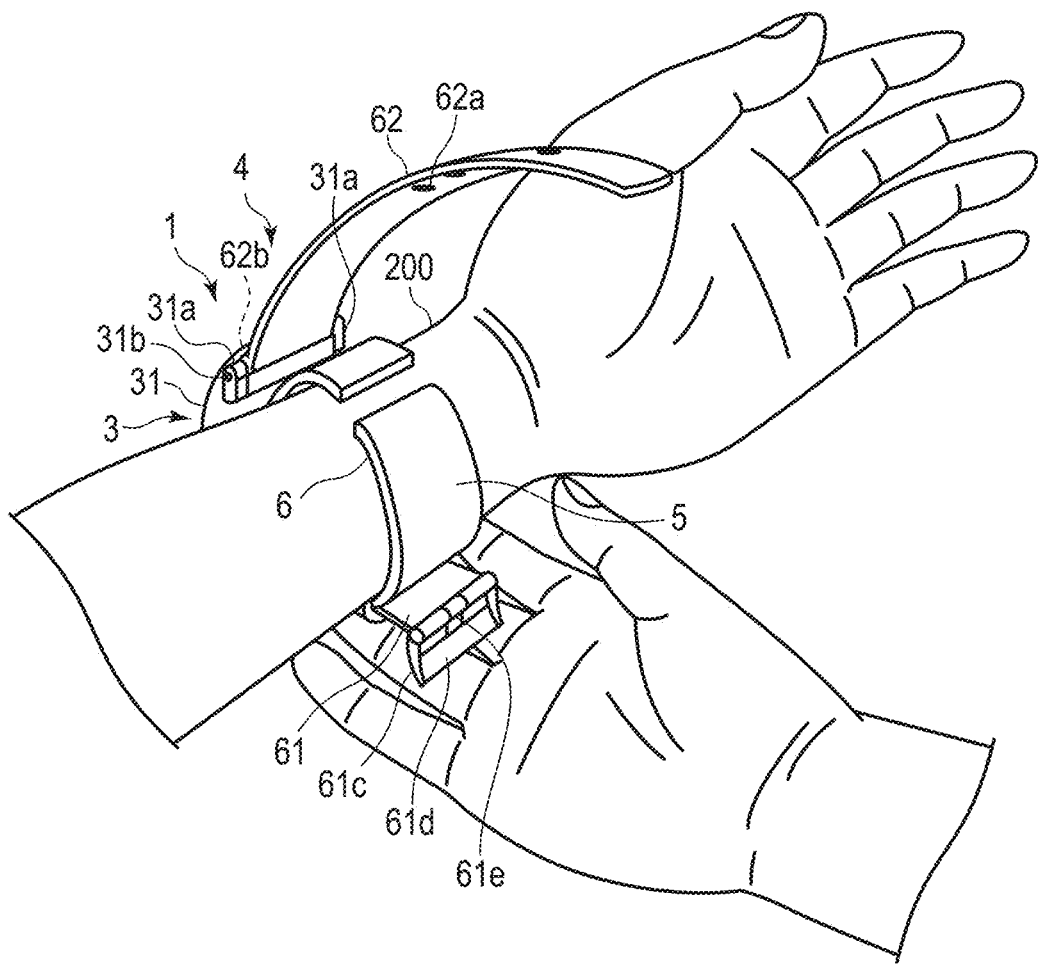
FIG. 17 is a perspective diagram showing an example in which the blood pressure measuring device is worn on a wrist.
Figure 18:
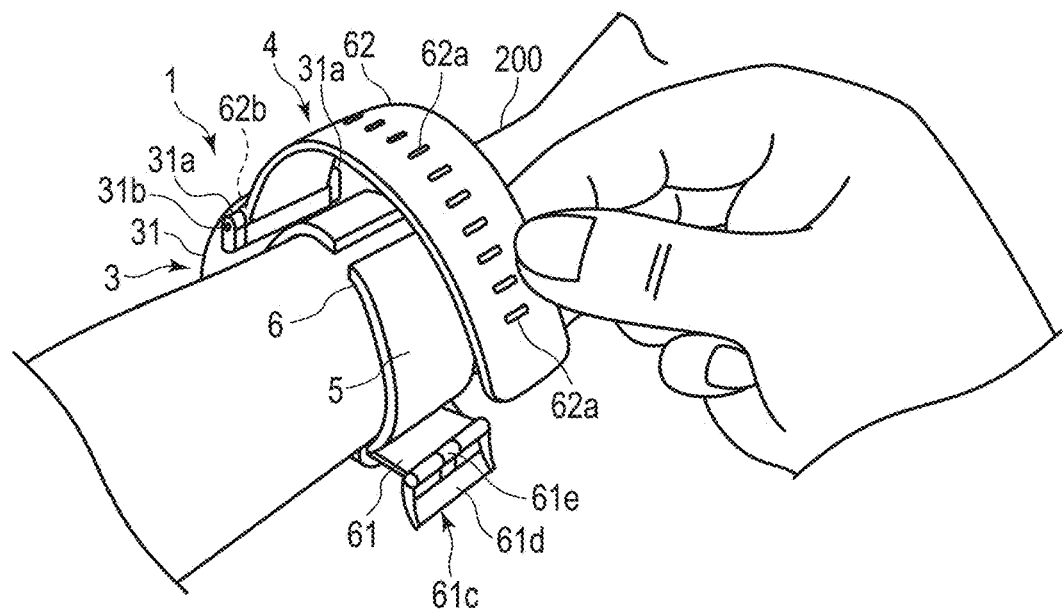
FIG. 18 is a perspective diagram showing an example in which the blood pressure measuring device is worn on a wrist.
Figure 19:
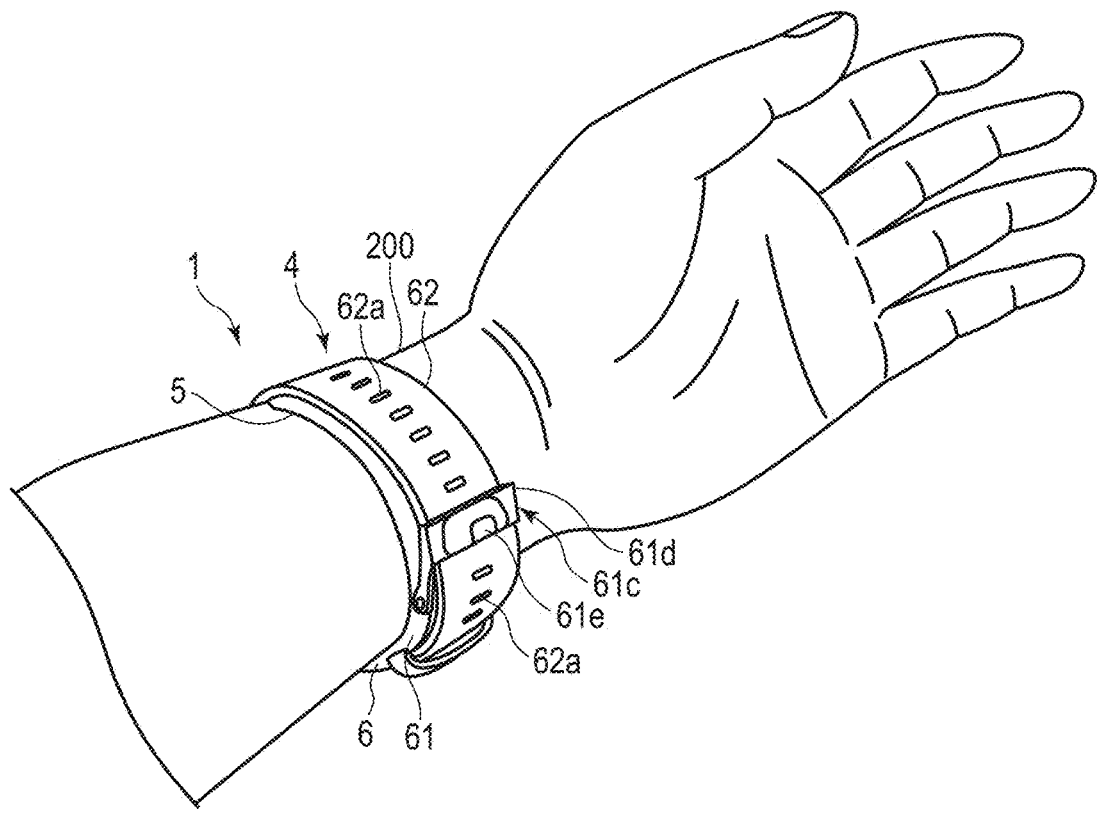
FIG. 19 is a perspective diagram showing an example in which the blood pressure measuring device is worn on a wrist.

Next, an example of measurement of blood pressure values using the blood pressure measuring device 1 will be described with reference to FIGS. 16 to 19. FIG. 16 is a flowchart showing an example of blood pressure measurement using the blood pressure measuring device 1, and shows both the operation of a user and the operation of the controller 55. FIGS. 17 to 19 show an example in which the user wears the blood pressure measuring device 1 on the wrist 200.

First, the user wears the blood pressure measuring device 1 on the wrist 200 (step ST1). As a specific example, the user, for example, inserts one of the wrists 200 into the curler 5, as shown in FIG. 17.

At this time, since the device main body 3 and the sensing cuff 73 are disposed at positions of the curler 5 opposed to each other in the blood pressure measuring device 1, the sensing cuff 73 is disposed in a region of the wrist 200 on the palmar side where the arteries 210 exist. Thus, the device main body 3 and the pulling cuff 74 are disposed on the dorsal side of the wrist 200. Next, the user passes the second strap 62 through the frame-shaped body 61d of the buckle 61c of the first strap 61 using the hand opposite to the hand on which the blood pressure measuring device 1 is placed, as shown in FIG. 18. Then, the user pulls the second strap 62, brings the member on the inner peripheral surface side of the curler 5, that is, the cuff structure 6, into close contact with the wrist 200, and inserts the prodding stick 61e into the small hole 62a. As a result, the first strap 61 and the second strap 62 are connected, and the blood pressure measuring device 1 is worn on the wrist 200, as shown in FIG. 19.

Next, the user operates the operation unit 13 to input a command corresponding to initiation of measurement of blood pressure values. The operation unit 13 in which the input operation of the command has been performed outputs an electric signal corresponding to initiation of measurement to the controller 55 (step ST2). Upon receiving the electric signal, the controller 55, for example, opens the first on-off valve 16A and closes the second on-off valve 16B, drives the pump 14, and supplies compressed air to the pressing cuff 71, the sensing cuff 73, and the pulling cuff 74 through the first flow passage 7a and the second flow passage 7b (step ST3). Thereby, the pressing cuff 71, the sensing cuff 73, and the pulling cuff 74 start to inflate.

The first pressure sensor 17A and the second pressure sensor 17B detect the pressures of the pressing cuff 71, the sensing cuff 73, and the pulling cuff 74, and output electric signals corresponding to the detected pressures to the controller 55 (step ST4). Based on the received electric signals, the controller 55 determines whether or not the pressures in the internal spaces of the pressing cuff 71, the sensing cuff 73, and the pulling cuff 74 reach a predetermined pressure for measuring blood pressure (step ST5). For example, when the internal pressures of the pressing cuff 71 and the pulling cuff 74 do not reach the predetermined pressure and the internal pressure of the sensing cuff 73 reaches the predetermined pressure, the controller 55 closes the first on-off valve 16A and supplies compressed air through the first flow passage 7a.

When the internal pressures of the pressing cuff 71 and the pulling cuff 74 and the internal pressure of the sensing cuff 73 all reach the predetermined pressure, the controller 55 stops driving the pump 14 (YES in step ST5). At this time, the pressing cuff 71 and the pulling cuff 74 are sufficiently inflated, and the inflated pressing cuff 71 presses the wrist 200 and the rubber plate 76, as shown in FIGS. 14 and 15. Since the pulling cuff 74 presses the curler 5 in a direction away from the wrist 200, the strap 4, the curler 5, and the device main body 3 move in a direction away from the wrist 200, and as a result, the pressing cuff 71, the rubber plate 76, the sensing cuff 73, and the flat plate 75 are pulled toward the wrist 200. In addition, when the strap 4, the curler 5, and the device main body 3 move in a direction away from the wrist 200 due to the inflation of the pulling cuff 74, the strap 4, the curler 5, and the device main body 3 move with the strap 4 and the curler 5 moving toward both sides of the wrist 200 to be in close contact with both sides of the wrist 200. Therefore, the strap 4 and the curler 5 in close contact with the skin of the wrist 200 pull the skin on both sides of the wrist 200 toward the dorsal side. The curler 5 may be configured to indirectly contact the skin of the wrist 200 via the sheet members 86 and 106, for example, as long as it can pull the skin of the wrist 200.

Further, the sensing cuff 73 is supplied with a predetermined amount of air so that the internal pressure thereof becomes a pressure required for measuring blood pressure, becomes inflated, and is then pressed toward the wrist 200 by the rubber plate 76 pressed by the pressing cuff 71. Therefore, the sensing cuff 73 presses the arteries 210 in the wrist 200 to occlude the arteries 210, as shown in FIG. 15.

For example, the controller 55 controls the second on-off valve 16B to repeatedly open and close the second on-off valve 16B or adjust the opening degree of the second on-off valve 16B, thereby increasing the pressure in the internal space of the pressing cuff 71. Based on the electric signal output from the second pressure sensor 17B in the pressurization process, the controller 55 obtains measurement results of blood pressure values, such as systolic blood pressure and diastolic blood pressure, a heart rate, and the like (step ST6). The controller 55 outputs an image signal corresponding to the obtained measurement results to the display 12. After the blood pressure measurement is completed, the controller 55 opens the first on-off valve 16A and the second on-off valve 16B.

Upon receiving the image signal, the display 12 displays the measurement results on a screen (step ST7). The user checks the measurement results by viewing the display 12. After the measurement is completed, the user removes the prodding stick 61e from the small hole 62a, removes the second strap 62 from the frame-shaped body 61d, and removes the wrist 200 from the curler 5, thereby removing the blood pressure measuring device 1 from the wrist 200.

In the blood pressure measuring device 1 according to the embodiment configured as described above, the pulling cuff 74 on the dorsal side of the curler 5 is inflated in a state where the strap 4 and the curler 5 as holders are in contact with the skin on both sides of the wrist 200 between the dorsal side and the palmar side. Therefore, in the blood pressure measuring device 1, when the pulling cuff 74 is inflated in a state where the strap 4 and the curler 5 are in contact with the skin on both sides of the wrist 200, the skin of the wrist 200 in the region contacted by the strap 4 and the curler 5 is pulled by the pulling cuff 74 together with the strap 4 and the curler 5. Since the skin of the wrist 200 on the palmar side of the wrist 200 is pulled thereby, sagging of the skin on the palmar side of the wrist 200, and the like are reduced, and the sensing cuff 73 comes into close contact with the skin on the palmar side of the wrist 200 on its surface. As a result, it is possible to suppress the generation of wrinkles and folds in the sensing cuff 73.

The blood pressure measuring device 1 can prevent the sensing cuff 73 from being wrinkled or folded by pressing the sensing cuff 73 with the pressing cuff 71. Also, since the blood pressure measuring device 1 is configured to tighten the wrist 200 with the strap 4 and press the curler 5, the strap 4 and the curler 5 as holders or the curler 5 come(s) reliably into contact with both sides of the wrist 200, therefore allowing the skin on both sides of the wrist 200 to be reliably pulled toward the dorsal side by the pulling cuff 74.

Further, since the rubber plate 76 extending in the circumferential direction of the wrist is arranged between the pressing cuff 71 and the sensing cuff 73, the rubber plate 76 transmits a pressing force from the pressing cuff 71 to the sensing cuff 73 in accordance with the shape of the wrist 200, thereby suppressing the generation of wrinkles and folds in the sensing cuff 73.

Since the flat plate 75 is provided between the curler 5 and the pressing cuff 71, the flat plate 75 can press the pressing cuff 71 and the sensing cuff 73 in the region of the wrist 200 where the tendon 220 exists, when pulled toward the wrist 200 by the pulling cuff 74. As a result, the blood pressure measuring device 1 can reduce variations in the pressure distribution of the region compressed by the sensing cuff 73 that occur when the wrist 200 is compressed, and can also suppress the generation of wrinkles and folds in the sensing cuff 73 by pressing the sensing cuff 73 with the tendon 220.

Since the flat plate 75 is provided between the curler 5 and the rubber plate 76, the flat plate 75 can press the rubber plate 76 and the sensing cuff 73 in the region of the wrist 200 where the tendon 220 exists, when the curler 5 is pulled toward the wrist 200 by the pulling cuff 74. Accordingly, the blood pressure measuring device 1 can suppress the generation of wrinkles and folds in the sensing cuff 73 by pressing the sensing cuff 73 with the tendon 220.

Since the rubber plate 76 is elastically deformable and is in close contact with the curler 5, the pressing cuff 71, and the flat plate 75 that are adjacent to the rubber plate 76, a gap between the curler 5 and the wrist 200 is filled, bringing the sensing cuff 73 into close contact with the wrist 200.

The blood pressure measuring device 1 is configured so that the thickness of the pulling cuff 74 in the inflation direction at the time of inflation is larger than the thickness of the pressing cuff 71 in the inflation direction at the time of inflation and the thickness of the sensing cuff 73 in the inflation direction at the time of inflation. With this configuration, when the pulling cuff 74 is inflated, it is possible to increase the amount of deformation of the strap 4 and the curler 5 in a direction in which the strap 4 and the curler 5 are in contact with both sides of the wrist 200, when the strap 4 and the curler 5 are deformed in a direction away from the wrist 200. As a result, the strap 4 and the curler 5 are in close contact with the portion of the wrist 200 between the dorsal side and the palmar side, and both sides of the wrist 200 between the dorsal side and the palmar side can be more reliably pulled toward the dorsal side. As a result, the skin of the wrist 200 on the palmar side facing the sensing cuff 73 is stretched, and the strap 4 and the curler 5 on the palmar side are pulled toward the wrist 200. Accordingly, the sensing cuff 73 is in suitably close contact with the surface of the skin in the region on the palmar side of the wrist 200 where the arteries 210 exist, and it is possible to further suppress the generation of wrinkles and folds in the sensing cuff 73.

As described above, according to the blood pressure measuring device 1 of the present embodiment, it is possible to suppress the generation of wrinkles and folds in the sensing cuff 73 by providing the pulling cuff 74 at a position facing the sensing cuff 73 of the curler 5.

Second Embodiment

Figure 20:
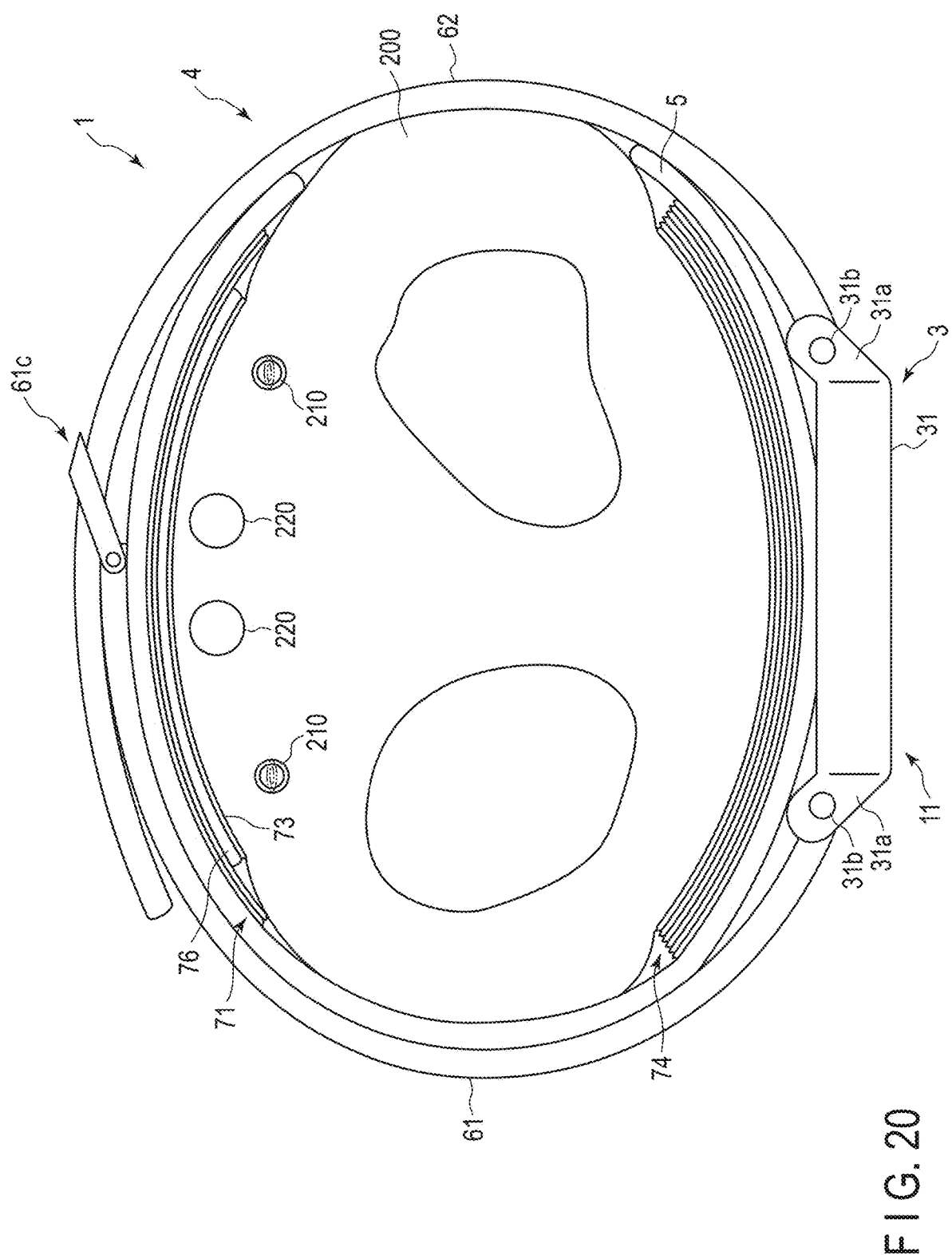
FIG. 20 is a plan view of a configuration of a cuff structure according to a second embodiment of the present invention in a state of being worn on a wrist.
Figure 21:
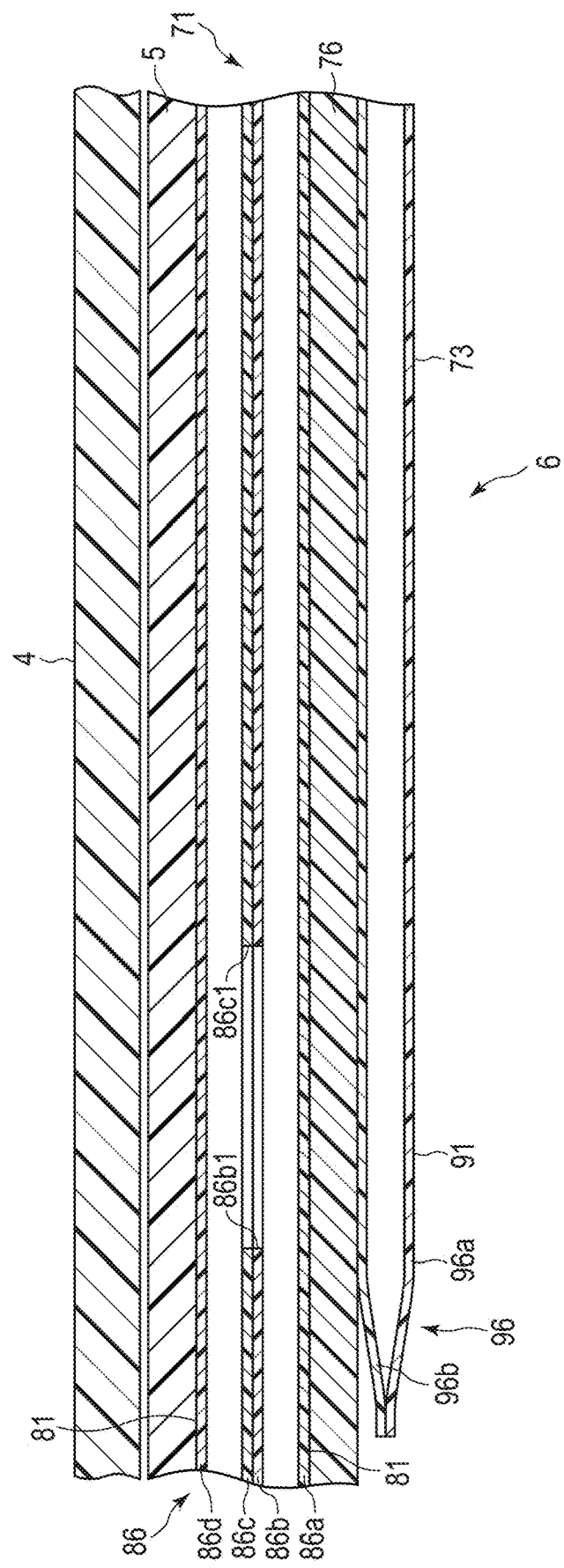
FIG. 21 is a cross-sectional view of configurations of the strap, the curler, and the cuff structure of the blood pressure measuring device.
Figure 23:
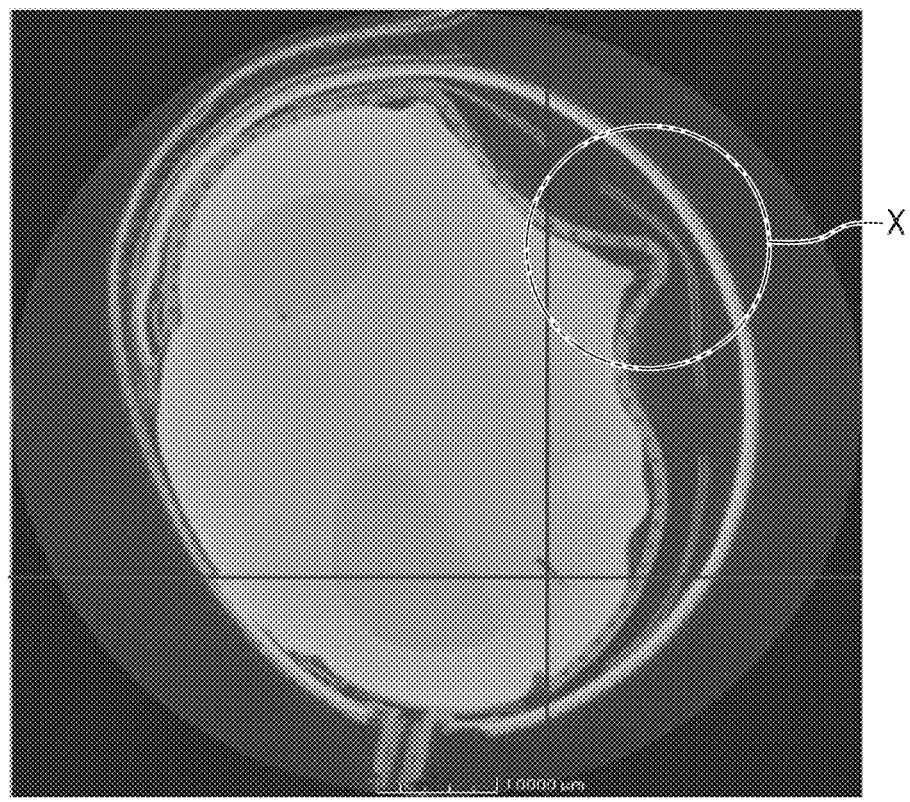
FIG. 23 is a cross-sectional image showing an example in which a conventional blood pressure measuring device is worn on a wrist and a cuff is inflated.

Next, a second embodiment of the blood pressure measuring device 1 will be described with reference to FIGS. 20 to 22. The blood pressure measuring device 1 does not include the flat plate 75 in the cuff structure 6. That is, the configuration of the second embodiment is achieved by removing the flat plate 75 from the configuration of the blood pressure measuring device 1 of the first embodiment described above; therefore, part of the configuration of the present embodiment identical to that of the blood pressure measuring device 1 of the first embodiment will be described using the same reference numerals, and the descriptions and figures thereof will be omitted as appropriate.

The blood pressure measuring device 1 according to the second embodiment exhibits the same effects as those of the blood pressure measuring device 1 according to the first embodiment, except those exhibited by the flat plate 75, and can suppress the generation of wrinkles and folds in the sensing cuff 73 by providing the pulling cuff 74 at a position facing the sensing cuff 73 of the curler 5.

The present invention is not limited to the embodiments described above. For example, the blood pressure measuring device 1 may be configured so that both the strap 4 and the curler 5 or only the curler 5 come(s) into contact with the wrist 200 at the time of blood pressure measurement. The curler 5 includes a member on the inner surface of the curler 5. That is, the blood pressure measuring device 1 may be configured so that the strap 4, the curler 5 or the member on the inner surface of the curler 5 can pull the skin of the wrist 200 when the pulling cuff 74 is inflated.

For example, in the blood pressure measuring device 1, the timing of opening and closing the first on-off valve 16A and the second on-off valve 16B at the time of blood pressure measurement can be suitably set. The example in which the blood pressure measuring device 1 calculates blood pressure based on a pressure measured in the process of pressurizing the pressing cuff 71 is described above; however, the present invention is not limited thereto. The blood pressure measuring device 1 may calculate blood pressure in the depressurization process or calculate blood pressure in both the pressurization process and the depressurization process.

Also, the above-described example shows the configuration of the pressing cuff 71 in which the air bag 81 is formed of each sheet member 86; however, the present invention is not limited thereto. For example, the air bag 81 may further include another configuration in order to control deformation or inflation of the pressing cuff 71.

The above-described embodiments are merely examples of the present invention in all respects. It goes without saying that various improvements and modifications can be made without departing from the scope of the present invention. In other words, in the implementation of the present invention, a specific configuration according to the embodiment may be adopted as appropriate.

That is, the present invention is not limited to the above-described embodiments and can be modified in various manners in practice without departing from the gist of the invention. The respective embodiments may be suitably combined to the extent possible, in which case a combined effect will be achieved. Furthermore, the above-described embodiments include various stages of invention, and various inventions can be derived by appropriate combinations of the plurality of disclosed elements.

REFERENCE SIGNS LIST

1. Blood pressure measuring device
3. Device main body
4. Strap
5. Curler
6. Cuff structure
7. Fluid circuit
7a. First flow passage
7b. Second flow passage
7c. Third flow passage
11. Case
12. Display
13. Operation unit
14. Pump
15. Flow passage section
16. On-off valve
16A. First on-off valve
16B. Second on-off valve
17. Pressure sensor
17A. First pressure sensor
17B. Second pressure sensor
18. Power supply unit
19. Vibration motor
20. Control substrate
31. Outer case
31a. Lug
31b. Spring rod
32. Windshield
33. Base
34. Flow passage cover
34a. Connected portion
35. Back cover
35a. Screw
36. Flow passage tube
41. Button
42. Sensor
43. Touch panel
51. Substrate
52. Acceleration sensor
53. Communication unit
54. Storage
55. Controller
61. First strap
61a. First hole
61b. Second hole
61c. Buckle
61d. Frame-shaped body
61e. Prodding stick
62. Second strap
62a. Small hole
71. Pressing cuff
73. Sensing cuff
74. Pulling cuff
75. Flat plate
75a. First plate member
75b. Second plate member
76. Rubber plate
81. Air bag
82. Tube
83. Connector
86. Sheet member
86a. First sheet member
86b. Second sheet member
86b1. Opening
86c. Third sheet member
86c1. Opening
86d. Fourth sheet member
91. Air bag
92. Tube
93. Connector
96. Sheet member
96a. Fifth sheet member
96b. Sixth sheet member
101. Air bag
102. Tube
103. Connector
106. Sheet member
106a. Seventh sheet member
106b. Eighth sheet member
106b1. Opening
106c. Ninth sheet member
106c1. Opening
106d. Tenth sheet member
106d1. Opening
106e. Eleventh sheet member
106e1. Opening
106f. Twelfth sheet member
106f1. Opening
106g. Thirteenth sheet member
106g1. Opening
106h. Fourteenth sheet member
106h1. Opening
106i. Fifteenth sheet member
106i1. Opening
106j. Sixteenth sheet member
106j1. Opening
106k. Seventeenth sheet member
106k1. Opening
1061. Eighteenth sheet member
200. Wrist
210. Artery
220. Tendon

The invention claimed is:

1. A blood pressure measuring device comprising:
a device main body;
a curler configured to bend along a circumferential direction of a wrist of a living body, including one end and another end separated from each other, configured to come into contact with a portion of the wrist at least between a dorsal side and a palmar side, and fixed to the device main body;
a strap connected to the device main body, configured to cover an outer surface of the curler, and configured to be mounted on the wrist;
a sensing cuff configured to be in a region of the wrist where arteries exist;
a rubber plate on a side of the sensing cuff nearer to the curler and configured to elastically deform;

a pressing cuff between the curler and the rubber plate and configured to press the sensing cuff;
a pulling cuff on a side of the curler configured to be nearer to the living body and on the dorsal side of the wrist; and
a flat plate between the curler and the pressing cuff and configured to be in a region of the wrist where a tendon exists.

2. The blood pressure measuring device according to claim 1, wherein
a thickness of the pulling cuff in a direction of inflating from the curler toward the wrist is larger than a thickness of the pressing cuff, and
the thickness of the pulling cuff in the direction of inflating from the curler toward the wrist is larger than a thickness of the sensing cuff.

* * * * *